US012599677B2

(12) United States Patent
Gordon et al.

(10) Patent No.: US 12,599,677 B2
(45) Date of Patent: Apr. 14, 2026

(54) TARGETED PH SENSITIVE LIPOSOMES

(71) Applicant: Northwestern University, Evanston, IL (US)

(72) Inventors: Leo I. Gordon, Winnetka, IL (US); Dong-Hyun Kim, Evanston, IL (US); Shuo Yang, Lisle, IL (US); Wooram Park, Evanston, IL (US); Taehoon Sim, Evanston, IL (US)

(73) Assignee: Northwestern University, Evanston, IL (US)

( * ) Notice: Subject to any disclaimer, the term of this patent is extended or adjusted under 35 U.S.C. 154(b) by 277 days.

(21) Appl. No.: 18/030,231

(22) PCT Filed: Oct. 4, 2021

(86) PCT No.: PCT/US2021/053409
§ 371 (c)(1),
(2) Date: Apr. 4, 2023

(87) PCT Pub. No.: WO2022/076324
PCT Pub. Date: Apr. 14, 2022

(65) Prior Publication Data

US 2023/0372532 A1 Nov. 23, 2023

Related U.S. Application Data

(60) Provisional application No. 63/087,828, filed on Oct. 5, 2020.

(51) Int. Cl.
*A61K 47/00* (2006.01)
*A61K 31/33* (2006.01)
(Continued)

(52) U.S. Cl.
CPC ........ *A61K 47/6911* (2017.08); *A61K 31/365* (2013.01); *A61K 47/62* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 7,491,693 | B2 | 2/2009 | Hubsch et al. |
| 2008/0306016 | A1 | 12/2008 | Mirkin et al. |

(Continued)

FOREIGN PATENT DOCUMENTS

| | | | |
|---|---|---|---|
| WO | WO 2009/018780 | A1 | 2/2009 |
| WO | WO 2018/053368 | A1 | 3/2018 |

OTHER PUBLICATIONS

Park et al., ACS Appl. Mater. Interfaces, 2016, vol. 8, pp. 12711-12719. (Year: 2016).*

(Continued)

*Primary Examiner* — Brian Gulledge
(74) *Attorney, Agent, or Firm* — Wolf, Greenfield & Sacks, P.C.

(57) ABSTRACT

Disclosed herein are synthetic nanoparticles, pharmaceutical compositions, kits, or methods for treating and/or preventing cancer. In some embodiments, the synthetic nanoparticles and/or pharmaceutical compositions comprises a pH sensitive liposome, an apolipoprotein, and andrographolide or derivative thereof. In some embodiments, the synthetic nanoparticles are delivered to a subject for treatment of cancer. In some embodiments, the cancer is T-cell lymphoma or B-cell lymphoma.

18 Claims, 10 Drawing Sheets

(51) Int. Cl.

| | |
|---|---|
| ***A61K 31/365*** | (2006.01) |
| ***A61K 47/62*** | (2017.01) |
| ***A61K 47/69*** | (2017.01) |
| ***A61P 35/00*** | (2006.01) |

(56) References Cited

U.S. PATENT DOCUMENTS

| | | | |
|---|---|---|---|
| 2014/0294927 | A1 | 10/2014 | Thaxton et al. |
| 2016/0193361 | A1 | 7/2016 | Thaxton et al. |
| 2017/0151339 | A1 | 6/2017 | White et al. |

OTHER PUBLICATIONS

International Search Report and Written Opinion for Application No. PCT/US2021/053409, mailed Jan. 14, 2022.

International Preliminary Report on Patentability for Application No. PCT/US2021/053409, mailed Apr. 20, 2023.

Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.

Faraji et al., Nanoparticles in cellular drug delivery. Bioorg Med Chem. Apr. 15, 2009;17(8):2950-62. doi: 10.1016/j.bmc.2009.02.043. Epub Feb. 26, 2009.

He et al., Discovery of siRNA lipid nanoparticles to transfect suspension leukemia cells and provide in vivo delivery capability. Mol Ther. Feb. 2014;22(2):359-370. doi: 10.1038/mt.2013.210. Epub Sep. 3, 2013.

Jones et al., Poly(2-alkylacrylic acid) polymers deliver molecules to the cytosol by pH-sensitive disruption of endosomal vesicles. Biochem J. May 15, 2003;372(Pt 1):65-75. doi: 10.1042/BJ20021945.

Kanamala et al., Mechanisms and biomaterials in pH-responsive tumour targeted drug delivery: A review. Biomaterials. Apr. 2016;85:152-67. doi: 10.1016/j.biomaterials.2016.01.061. Epub Jan. 29, 2016.

Ling et al., pH-sensitive nanoformulated triptolide as a targeted therapeutic strategy for hepatocellular carcinoma. ACS Nano. Aug. 26, 2014;8(8):8027-39. doi: 10.1021/nn502074x.

Liu et al., Effects of pH-sensitive chain length on release of doxorubicin from mPEG-b-PH-b-PLLA nanoparticles. Int J Nanomedicine. 2012;7:4433-46. doi: 10.2147/IJN.S32053. Epub Aug. 14, 2012.

Oku et al., Low pH induced membrane fusion of lipid vesicles containing proton-sensitive polymer. Biochemistry. Dec. 15, 1987;26(25):8145-50. doi: 10.1021/bi00399a019.

Paliwal et al., A review of mechanistic insight and application of pH-sensitive liposomes in drug delivery. Drug Deliv. May 2015;22(3):231-42. doi: 10.3109/10717544.2014.882469. Epub Feb. 13, 2014.

Park et al., Acidic pH-Triggered Drug-Eluting Nanocomposites for Magnetic Resonance Imaging-Monitored Intra-arterial Drug Delivery to Hepatocellular Carcinoma. ACS Appl Mater Interfaces. May 25, 2016;8(20):12711-9. doi: 10.1021/acsami.6b03505. Epub May 16, 2016.

Ranganathan et al., Nanomedicine: towards development of patient-friendly drug-delivery systems for oncological applications. Int J Nanomedicine. 2012;7:1043-60. doi: 10.2147/IJN.S25182. Epub Feb. 23, 2012.

Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.

PCT/US2021/053409, Jan. 14, 2022, International Search Report and Written Opinion.

PCT/US2021/053409, Apr. 20, 2023, International Preliminary Report on Patentability.

Ku et al., Mitochondria-selective photodynamic tumor therapy using globular PEG nanoparticles. Macromol Res. Jun. 22, 2016;24(7):634-9. doi: 10.1007/s13233-016-4090-9.

Lee et al., A feasibility study of a pH sensitive nanomedicine using doxorubicin loaded poly(aspartic acid-graft-imidazole)-block-poly(ethylene glycol) micelles. J Mater Chem B. Nov. 28, 2013;2(9):1152-9. doi: 10.1039/C3TB21379J.

Moku et al., Delivering anti-cancer drugs with endosomal pH-sensitive anti-cancer liposomes. Biomater Sci. Jan. 25, 2016;4(4):627-38. doi: 10.1039/C5BM00479A.

Yang et al., pH-Sensitive Liposomes for Intracellular and Tumour Targeted Drug Delivery. In: Liposomes: Historical, Clinical and Molecular Perspectives. Jun. 2017. Pearson, Ed. Chapter 5:135-70.

* cited by examiner

TARGETED PH SENSITIVE LIPOSOMES

RELATED APPLICATIONS

This application is a national stage filing under 35 U.S.C. § 371 of international application No. PCT/US2021/053409, filed Oct. 4, 2021, which claims the benefit under 35 U.S.C. § 119 (e) of U.S. application No. 63/087,828, filed Oct. 5, 2020. The contents of these applications are incorporated herein by reference in their entirety.

BACKGROUND

Lymphoma is cancer occurring in lymphocytes. Non-Hodgkin lymphoma, which show the absence of Reed-Stenberg cells, is the most common type lymphoma observed in patients, accounting for ~90% of the cases. Patients with Non-Hodgkin lymphoma exhibit a 10-year overall relative survival rate. Among Non-Hodgkin lymphoma, diffuse large B-cell lymphoma (DLBCL) is the most common type showing an aggressive tumor growth (www.cancerresearch.org). Even though chemotherapy and immunotherapy using monoclonal antibodies have shown therapeutic effects on lymphoma, some patients showed no improvement due to various reasons including the genetic subtypes. See, Armitage, J. O., et al., Non-hodgkin lymphoma. The Lancet, 2017. 390(10091): p. 298-310.; and Schmitz, R., et al., Genetics and pathogenesis of diffuse large B-cell lymphoma. New England journal of medicine, 2018. 378(15): p. 1396-1407. Combination therapy including CHOP (cytoxan, adriamycin, vincristine, prednisolone) and R-CHOP (Rituximab with CHOP) are standard treatments for DLBCL, though diverse side effects have been a clinical hurdle for patient recovery (www.cancer.org).

SUMMARY

The present disclosure is based, at least in part, on compositions, kits, and methods related to a synthetic nanoparticle comprising a pH sensitive liposome, comprising an apolipoprotein and andrographolide, that are useful in delivering andrographolide to subjects in need thereof. For example, without limitation, the synthetic nanoparticles may be that targets a cell surface receptor scavenger receptor B-1 (e.g., SR-B1). Further, due to the pH sensitivity of the liposome, the synthetic nanoparticle is more susceptible to delivering its payload (e.g., therapeutic, andrographolide), in a target environment, or in other words an local environment which due to the disease or disorder has a pH which is different than the pH of the same environment absent the disease or disorder (e.g., cancer cell microenvironment, stroke microenvironment).

In some aspects, the disclosure relates to a synthetic nanoparticle comprising: (a) a pH sensitive liposome comprising a lipid layer comprising at least one pH sensitive lipid; (b) an apolipoprotein in contact with the lipid layer; and (c) a drug having a low water solubility encapsulated within the liposome.

In some embodiments, the apolipoprotein is apolipoprotein A-I (Apo-A1), apolipoprotein A-II, or apolipoprotein E.

In some embodiments, the pH sensitive liposome comprises a pH sensitive phospholipid. In some embodiments, the pH sensitive liposome comprises octadecylamine-p (API-L-ASP)10 (pH-ADT).

In some embodiments, the pH sensitive liposome further comprises egg-phosphatidylcholine, lipids egg-phosphatidylcholine (EPC), 1,2-distearoyl-sn-glycero-3-phosphoethanolamine-N-[methoxy (polyethylene glycol)-2000] (DSPE-PEG2000), DSPE-PEG-Cy 5, and/or a combination thereof.

In some embodiments, the synthetic nanoparticle has a largest cross-sectional dimension of less than or equal to 1000 nanometers (nm). In some embodiments, the synthetic nanoparticle has a largest cross-sectional dimension of less than or equal to 500 nanometers (nm). In some embodiments, the synthetic nanoparticle has a largest cross-sectional dimension of less than or equal to 200 nanometers (nm).

In some embodiments, the drug is andrographolide and/or derivative thereof.

In some embodiments, the synthetic nanoparticle has a zeta potential between about 0 and about −5, 0 and about −4, or about −1 and about −3 in a solution of about pH 7.4. In some embodiments, the synthetic nanoparticle has a zeta potential between about 1 and about 3 or about 2 and about 3 in a solution of about pH 6.5.

In some embodiments, the synthetic nanoparticle binds to scavenger receptor B-1 (SR-B1).

In some embodiments, the synthetic nanoparticle further comprises a nanostructure core on the interior of the pH sensitive liposome. In some embodiments, the nanostructure core comprises an organic nanostructure core. In some embodiments, the nanostructure core comprises an inorganic nanostructure core. In some embodiments, the nanostructure core comprises a gold nanostructure core.

In some aspects, the disclosure relates to a method of treating a subject who has cancer, comprising, administering an effective amount of any of the synthetic nanoparticles as described herein.

In some embodiments, the cancer is selected from: B-cell lymphoma and T-cell lymphoma.

In some embodiments, the subject is a mammal. In some embodiments, the subject is a human.

In some aspects, the disclosure relates to a method of reducing, in a population of cells, the number of live cancer cells, the method comprising: contacting the cancer cells with any of the synthetic nanoparticles as described herein, wherein the synthetic nanoparticle is in an effective amount to induce apoptosis in the cancer cells. In some embodiments, the synthetic nanoparticles are any of the synthetic nanoparticles as described herein.

In some embodiments, the cancer is selected from: B-cell lymphoma and T-cell lymphoma. In some embodiments, the cancer is comprised of SR-B1 positive cancer cells. In some embodiments, the cancer is comprised of SR-B1 negative cancer cells.

In some embodiments, the drug is a chemotherapeutic agent. In some embodiments, the drug is Andro or derivatives thereof.

In some embodiments, the effective amount of the nanoparticle comprises a sub-therapeutic amount of a drug, wherein a subtherapeutic amount comprises an amount that is less than a minimal amount required for producing a therapeutic result in a buffer or alcohol carrier.

In some aspects, the disclosure relates to a method of treating a subject who has a stroke or has suffered from a stroke, comprising, administering an effective amount of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticles are any of the synthetic nanoparticles as described herein.

In some embodiments, the nanoparticle is administered to the subject within 1 month of the stroke in the subject. In some embodiments, the nanoparticle is administered to the subject within 1 week of the stroke in the subject. In some embodiments, the nanoparticle is administered to the subject within 1 day of the stroke in the subject. In some embodiments, the nanoparticle is administered to the subject within 12 hours of the stroke in the subject.

In some embodiments, the drug comprises an anti-inflammatory agent. In some embodiments, the drug is selected from the group consisting of anti-platelet drugs, anticoagulants, tissue plasminogen activator, statins, and blood pressure drugs.

In some aspects, the disclosure relates to a method for modulating an immune response in a subject, comprising, administering an effective amount to modulate an immune response of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticles are any of the synthetic nanoparticles as described herein.

In some embodiments, the synthetic nanoparticle enhances cytotoxic T cells, natural killer (NK) cells, phagocytosis, antibody-dependent cell-mediated cytotoxicity (ADCC), or a combination thereof.

In some aspects, the disclosure relates to a method of inhibiting viral activity in a subject, comprising, administering an effective amount to inhibit viral activity of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticles are any of the synthetic nanoparticles as described herein.

In some embodiments, the synthetic nanoparticle enhances cytotoxic T cells, natural killer (NK) cells, phagocytosis, antibody-dependent cell-mediated cytotoxicity (ADCC), or a combination thereof.

In some embodiments, the subject has been infected by, or is at risk of being infected by, influenza A virus, hepatitis B virus, hepatitis C virus, Herpes simplex 1 virus, Epstein-Barr virus, human papilloma virus, human immunodeficiency virus, and/or Chikungunya virus.

In some aspects, the disclosure relates to a method of increasing macrophage activity in a subject, comprising, administering an effective amount to inhibit viral activity of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticles are any of the synthetic nanoparticles as described herein.

In yet other embodiments or aspects the invention encompasses any of the paragraphs listed under the heading "other embodiments."

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

FIG. 2A shows particle size distribution by DLS at pH 7.4 and 6.5. FIG. 2B shows zeta potential at pH 7.4 and 6.5 of pH-ALs.

FIG. 3A shows the pH-dependent drug release at different pH conditions (pH 7.4 and 6.5). FIG. 3B shows endosomal disruption by confocal microscopy.

DETAILED DESCRIPTION

The present invention relates to compositions (e.g., synthetic nanoparticles) that are useful for delivering therapeutics to a subject. The synthetic nanoparticles of the present disclosure improve the bioavailability and toxicity profile of the therapeutics as well as permit the targeting of the therapeutics to cells of interest (e.g., diseased (e.g., cancer), target cells), when administered to a subject.

Additionally, the compositions of the present disclosure comprise pH sensitive liposomes which contribute to the high potential of delivering the therapeutic (e.g., andrographolide) to a target (e.g., due to pH-dependent liposome, the drug releases in unique cancer microenvironments). This property can be tailored, for example to provide precise pH sensitivity for the endosomal pH, moiety with a selected pKa can be used to enabling higher intracellular drug release and following enhanced cytotoxicity.

These synthetic nanoparticles may also be assembled to create an affinity of the composition (e.g., synthetic nanoparticles) for specific cell surface receptors (e.g., Scavenger receptor type B-1 (SR-B1)). Through their interaction with these cell surface receptors (e.g., SR-B1), the synthetic nanoparticles can direct their payload (e.g., therapeutic, andrographolide) to targeted locations (e.g., cells) and therefore can be used as a prophylactic or treatment for target cells (e.g., diseased (e.g., cancer)) expressing the cell surface receptor (e.g., SR-B1). These findings have tremendous implications for prevention of a plethora of diseases associated with andrographolide sensitivity and/or SR-B1 expression.

Figure 1:
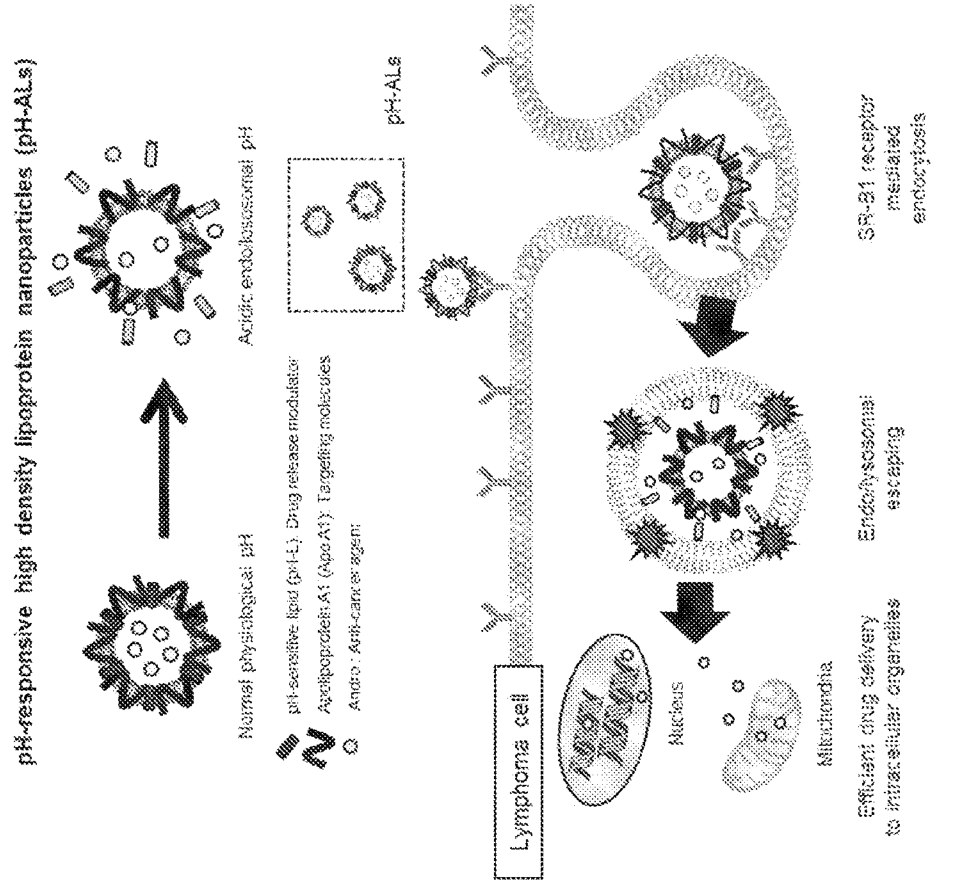
FIG. 1 shows an illustration of pH-sensitive andrographolide/Apo A1 loaded liposome for B cell and T cell lymphoma treatments.

The combination particle of the invention includes a pH sensitive liposome layer of lipids, optionally a bilayer of lipids, surrounding a drug, wherein an apolipoprotein is incorporated into the liposome. An exemplary illustration of a pH-sensitive liposome-drug (i.e., andrographolide)-apolipoprotein (i.e., Apo A1) construct is shown in FIG. 1 and is referred to as a pH-responsive high density lipoprotein nanoparticle (pH-AL). A schematic of a pH-AL under normal physiological pH is shown on the left. Apolipoprotein and pH sensitive lipid are incorporated into a lipid bilayer. Upon exposure to acidic endosomal pH the lipids and drug are released. The bottom panel demonstrates how the apolipoprotein targets the SR-B1 on the cell surface, triggering SR-B1 mediated endocytosis. Once the particle is in the endosome or lysosome drug is released in response to acidic pH conditions, leading to effective intracellular delivery of the drug.

SR-B1 is expressed by lymphoma cells. Targeting these cells with a delivery modality which contains a therapeutic (e.g., andrographolide) causes cell death and treatment of the disorder (e.g., lymphoma). The synthetic nanoparticles of the invention are uniquely designed to target SR-B1, deliver andrographolide, and instigate apoptosis in lymphoma cells. Data disclosed herein demonstrates that the synthetic nanoparticles effect cell death in lymphoma cells.

The size and amphiphilic nature of the surface chemical composition of the synthetic nanoparticles enables them to engage and tightly bind to SR-B1, expressed by target cells, to modulate apoptosis. The synthetic nanoparticles and administration thereof, have a tremendous number of applications (e.g., preventing/treating diseases associated with expression (e.g., increased expression) of SR-B1), cancer). Cancer which these synthetic nanoparticles may be useful in treating include, any cancer in which SR-B1 is expressed, such as, without limitation, B-cell lymphoma and T-cell lymphoma.

Synthetic Nanoparticles

The synthetic nanoparticles may be any nanoparticle having the properties of being pH sensitive and conveying the ability to carry a drug having a low water solubility encapsulated within the liposome (e.g., andrographolide, or derivative thereof). Additionally, the synthetic nanoparticle may comprise the property of being able to bind to a cell surface receptor such as SR-B1 (e.g., by containing apolipoprotein). In some embodiments, the synthetic nanoparticles comprise a pH sensitive liposome (which may be referred to herein simply as the "liposome"). In some embodiments, a liposome comprises at least one lipid. In some embodiments, a lipid comprises a phospholipid. In some embodiments, the lipid is a pH sensitive lipid or polymer. In some embodiments, the pH sensitive lipid or polymer comprises poly acid lipids, carboxylic acid, sulfonic acid, phosphonic acids, boronic acids, a polymers (e.g., chitosan, dextran, hyaluronic acid), cationic molecules, or a combination thereof. In some embodiments, a liposome comprises octadecylamine-p(API-L-ASP)$_{10}$ (pH-ADT). The liposome may comprise a single lipid layer or may comprise a lipid comprised of multiple layers (e.g., bilayer, multi-layer). In some embodiments, the lipid layer may be cross-linked. Crosslinking of components of the lipid layer, for example, can modulate transport across the lipid layer, or between an area exterior to the lipid layer and an area interior of the lipid layer. For example, relatively high amounts of crosslinking may allow certain small, but not large, molecules to pass into or through the lipid layer, whereas relatively low or no crosslinking can allow larger molecules to pass into or through the lipid layer.

In some embodiments, the pH sensitive liposome comprises additional lipids. For example, the pH sensitive liposome may comprise egg-phosphatidylcholine, lipids egg-phosphatidylcholine (EPC), 1,2-distearoyl-sn-glycero-3-phosphoethanolamine-N-[methoxy (polyethylene glycol)-2000] (DSPE-PEG2000), DSPE-PEG-Cy 5, and/or a combination thereof.

In some embodiments, the liposome of the synthetic nanoparticle is coated with apolipoprotein. An example of a suitable apolipoprotein that may associate with a liposome described herein is an apolipoprotein, such as apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Additionally, or alternatively, a structure described herein may include one or more peptide analogues of an apolipoprotein, such as one described above. A structure may include any suitable number of, e.g., at least 1, 2, 3, 4, 5, 6, 10, or more, apolipoproteins or analogues thereof. In certain embodiments, a structure includes 1-6 apolipoproteins. Of course, other proteins (e.g., non-apolipoproteins) can also be included in synthetic nanoparticles as described herein. In some embodiments, the apolipoprotein is apolipoprotein A-1 (Apo-A1).

In some embodiments, the synthetic nanoparticle comprises a therapeutic (e.g., payload to effect treatment). It can be envisioned that any number of therapeutics could be used with the apolipoprotein coated pH sensitive liposomes. For example, without limitation, andrographolide, or a derivative thereof, may be selected as a therapeutic. Andrographolide (also referred to herein as Andro) is a diterpenoid lactone isolated from Andrographis paniculate, which have been shown anti-inflammatory, antihypertensive, antiviral, and immune-stimulant effect. Recently, it has been shown to inhibit cancer cell proliferation and induce ROS-dependent apoptosis through mitochondrial pathways in various lymphoma cell lines including Burkitt p53-mutated Ramos cell line, the mantle cell lymphoma (MCL) line Granta, the follicular lymphoma (FL) cell line HF-1, and the diffuse large B-cell lymphoma (DLBCL) cell line SUDHL4, as well as primary cells from patients with FL, DLBCL, and MCL. However, andrographolide exhibits low solubility in water, reducing its bioavailability. See, Chen, M., C. Xie, and L. Liu, Solubility of andrographolide in various solvents from (288.2 to 323.2) K. Journal of Chemical & Engineering Data, 2010. 55(11): p. 5297-5298.; Meng, W., et al., Stability of active ingredients of traditional Chinese medicine (TCM). Natural product communications, 2009. 4(12): p. 1934578X0900401229; and Piazzini, V., et al., Stealth and cationic nanoliposomes as drug delivery systems to increase andrographolide BBB permeability. Pharmaceutics, 2018. 10(3): p. 128.

The term "derivative," as may be used herein, carries the meaning as would be ascribed to such term by the skilled artisan, but generally is known to refer to any compound having the same or a similar core structure to the compound of which it is a derivative (e.g., andrographolide), but having at least one structural difference, including substituting, deleting, and/or adding one or more atoms or functional groups. The term derivative does not exclusively mean that the derivative is synthesized from the parent compound either as a starting material or intermediate, although it does encompass such scenarios. The term derivative can include prodrugs and/or metabolites of the parent compound (e.g., andrographolide). Any method of making, developing, and/or synthesizing derivatives can be used herein, and is envisioned as embodied by the present disclosure and definition herein.

Andrographolide derivatives include those disclosed in WO 2009/018780 including those having the following structure:

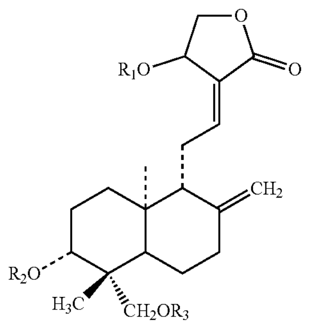

wherein $R_1$, $R_2$ and $R_3$ are the same or different groups selected from hydrogen, substituted or unsubstituted organic acid radicals, inorganic acid radicals, alkyl, aryl or heteroaryl, and at least one of $R_1$, $R_2$ and $R_3$ is R-lipoic acid, S-lipoic acid or a racemic lipoic acid, or its corresponding dihydrolipoic acid, or a NI-acetyl cysteine radical.

Andrographolide derivatives also include those disclosed in Wang, B., et al, Med Chem. 2012 March; 8(2):293-8; Li, F., Discovery and preliminary SAR of 14-aryloxy-andrographolide derivatives as antibacterial agents with immunosuppressant activity, RSC Adv., 2018, 8, 9440; Liu Y. et al., Synthesis of thioether andrographolide derivatives and their inhibitory effect against cancer cells, Med. Chem. Commun., 2017, 8, 1268; Peng, Y., SAR studies of 3,14,19-derivatives of andrographolide on anti-proliferative activity to cancer cells and toxicity to zebrafish: an in vitro and in vivo study, RSC Adv., 2015, 5, 22510; Sheng, D., et al, Differential in vitro and in vivo anti-angiogenic activities of acetal and ketal andrographolide derivatives in HUVEC and zebrafish models; RSC Adv., 2016, 6.

The formulations of the invention are useful for enhancing the delivery of andrographolide. For instance, formulating the andrographolide into pH sensitive liposomes attenuates the low solubility, promoting the andrographolide's release in the target microenvironment. As used herein, a target microenvironment refers to a local environment which due to the disease or disorder has a pH which is different than the pH of the same environment absent the disease or disorder (e.g., cancer cell microenvironment, stroke microenvironment). For example, without limitation, a cancer cell microenvironment (e.g., local area of a tumor or cancer cell) and/or a microenvironment near the occurrence of a stroke in a subject. Additionally, cellular processes which effectuate a local pH change in a subject may be targeted using the pH sensitive liposomes and synthetic nanoparticles of the present disclosure. Such uses and methods are envisioned by the present disclosure and embodied herein.

The synthetic nanoparticle may have a largest cross-sectional dimension (or, sometimes, a smallest cross-section dimension, or diameter) of, for example, less than or equal to 1200 nanometers (nm). In some embodiments, the largest cross-sectional dimension is less than or equal to 1000 nanometers (nm). In some embodiments, the largest cross-sectional dimension is less than or equal to 800 nanometers (nm). In some embodiments, the largest cross-sectional dimension is less than or equal to 600 nanometers (nm). In some embodiments, the largest cross-sectional dimension is less than or equal to 500 nanometers (nm). In some embodiments, the largest cross-sectional dimension is greater than or equal to 50 nanometers (nm). In some embodiments, the largest cross-sectional dimension is greater than or equal to 80 nanometers (nm). In some embodiments, the largest cross-sectional dimension is greater than or equal to 100 nanometers (nm).

The components of a synthetic nanoparticle may be charged, e.g., to impart a charge on the surface of the nanoparticle, or it may remain uncharged. In some embodiments, the surface of the synthetic nanoparticle may have a zeta potential between about 0 and about −5 in a solution of about pH 7.4. In some embodiments, the surface of the synthetic nanoparticle may have a zeta potential between about 0 and about −4 in a solution of about pH 7.4. In some embodiments, the surface of the synthetic nanoparticle may have a zeta potential between about 1 and about −3 in a solution of about pH 7.4. In some embodiments, the surface of the synthetic nanoparticle may have a zeta potential between about −1 and about −3 in a solution of about pH 7.4. In some embodiments, the surface of the synthetic nanoparticle may have a zeta potential between about 1 and about 3 in a solution of about pH 6.5. In some embodiments, the surface of the synthetic nanoparticle may have a zeta potential between about 2 and about 3 in a solution of about pH 6.5.

The synthetic nanoparticle may comprise a nanostructure core coated by the liposome, and an apolipoprotein associated with the lipid layer of the liposome, wherein the synthetic nanoparticle contains a therapeutic (e.g., andrographolide). Examples of synthetic nanoparticle useful for the present purposes are described below. In some embodiments, the synthetic nanoparticle may be a synthetic cholesterol binding nanostructure, i.e., a biomimic of mature, spherical HDL, e.g., in terms of the size, shape, surface chemistry and/or function of the structures. Control of such features may be accomplished at least in part by using a synthetic template for the formation of the synthetic nanoparticle. For example, high-density lipoprotein synthetic nanoparticles (HDL-NP) may be formed by using a solid core NP such as a gold nanoparticle (Au—NP) (or other suitable entity or material) as a synthetic template to which other components (e.g., lipids, proteins, etc.) can be added.

In some aspects, the synthetic nanoparticle of the present disclosure, comprises a core coated with phospholipids and/or pH sensitive lipids encapsulating a drug having a low water solubility encapsulated within the nanoparticle. In some embodiments, a drug having a low water solubility is andrographolide, or derivative thereof. In some embodiments, the core is a nanoparticle which includes a surface to which one or more components can be optionally attached. For instance, in some cases, the nanoparticle is coated with phospholipids and/or pH sensitive lipids creating a coating, which coating includes an inner surface and an outer surface. The coating may further comprise additional components (e.g., other lipids, polymers, molecules). The coating may be formed, at least in part, of one or more components, such as a plurality of phospholipids, which may optionally associate with one another and/or with surface of the core. For example, components may be associated with the core by being covalently attached to the core, physiosorbed, chemisorbed, or attached to the core through ionic interactions, hydrophobic and/or hydrophilic interactions, electrostatic interactions, van der Waals interactions, or combinations thereof. In some embodiments, the core includes a gold nanoparticle and the coating is attached to the core through a gold-thiol bond.

It should be understood that a coating that surrounds a core need not completely surround the core, although such embodiments may be possible. For example, the coating may surround at least 50% (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more) of the surface area of a core. In some cases, the coating substantially surrounds a core. In other cases, the coating completely surrounds a core. The components of the coating may be distributed evenly across a surface of the core in some cases, and unevenly in other cases. For example, the coating may include portions (e.g., holes) that do not include any material in some cases. If desired, the coating may be designed to allow penetration and/or transport of certain molecules and components into or out of the coating, but may prevent penetration and/or transport of other molecules and components into or out of the coating.

In some embodiments, the coating comprises an inner leaflet (e.g., layer) and an outer leaflet (e.g., layer). The inner lipids may be pH sensitive and/or may comprise thiol or disulfide headgroups in order to covalently attach the phospholipid to the core (e.g., gold core). The outer leaflet may comprise pH sensitive lipids and/or phospholipids of other headgroups. For example, without limitation, several lipids and/or combinations of lipids can be used to generate the outer leaflet, including, but not limited to: 1,2-dipalmitoyl-sn-glycero-3-phosphocholine (DPPC), 1,2-dioleoyl-sn-glycero-3-phosphocholine (DOPC), 1,2-dipalmitoyl-sn-glycero-3-phosphoethanolamine (16:0), 1,2-distearoyl-sn-glycero-3-phosphoethanolamine (18:0 PE), sphingomyelin, 1,2-dioleoyl-3-trimethylammonium-propane (DOTAP), and/or a ganglioside. In some embodiments, a ganglioside is monosialotetrahexosylganglioside (GM1; IUPAC-(2S,4S,5R,6R)-5-acetamido-2-[(2S,3R,4R,5S,6R)-5-[(2S,3R,4R,5R,6R)-3-acetamido-5-hydroxy-6-(hydroxymethyl)-4-[(2R,3R,4S,5R,6R)-3,4,5-trihydroxy-6-(hydroxymethyl)oxan-2-yl]oxyoxan-2-yl]oxy-2-[(2R,3S,4R,5R,6R)-4,5-dihydroxy-2-(hydroxymethyl)-6-RE,2S,3R)-3-hydroxy-2-(octadecanoylamino)octadec-4-enoxy]oxan-3-yl]oxy-3-hydroxy-6-(hydroxymethyl)oxan-4-yl]oxy-4-hydroxy-6-[(1R,2R)-1,2,3-trihydroxypropyl]oxane-2-carboxylic acid), monosialoganglioside (GM2; IUPAC-(2S,4S,5R,6R)-5-acetamido-2-[(2S,3R,4R,5S,6R)-5-[(2S,3R,4R,5R,6R)-3-acetamido-4,5-dihydroxy-6-(hydroxymethyl)oxan-2-yl]oxy-2-[(2R,3S,4R,5R,6R)-4,5-dihydroxy-2-(hydroxymethyl)-6-RE,2S,3R)-3-hydroxy-2-(octadecanoylamino)octadec-4-enoxy]oxan-3-yl]oxy-3-hydroxy-6-(hydroxymethyl)oxan-4-yl]oxy-4-hydroxy-6-[(1R,2R)-1,2,3-trihydroxypropyl]oxane-2-carboxylic acid), monosialodihexosylganglioside (GM3; IUPAC-(2S,4S,5R)-5-acetamido-2-[(2S,3R,4S,5S,6R)-2-[(2R,3S,4R,6R)-4,5-dihydroxy-2-(hydroxymethyl)-6-RE,2S,3R)-3-hydroxy-2-(octadecanoylamino)octadec-4-enoxy]oxan-3-yl]oxy-3,5-dihydroxy-6-(hydroxymethyl)oxan-4-yl]oxy-4-hydroxy-6-[(1R,2R)-1,2,3-trihydroxypropyl]oxane-2-carboxylic acid), lipids containing phosphatidyl glycerol headgroups, phosphatidyl ethanolamine (DPPE), lipids containing biotin headgroups, or a combination thereof.

In some embodiments, the nanostructure core is less than or equal to about 5 nm in diameter. In some embodiments, the core is less than or equal to about 10 nm in diameter. In some embodiments, the core is less than or equal to about 15 nm in diameter. In some embodiments, the core is less than or equal to about 30 nm in diameter. In some embodiments, the core is less than or equal to about 60 nm in diameter. In some embodiments, the core is greater than or equal to about 60 nm in diameter.

In embodiments the core may be formed from any suitable material. In some embodiments, the core is formed from gold (e.g., made of gold (Au)). In some embodiments, the core is formed of a synthetic material (e.g., a material that is not naturally occurring, or naturally present in the body). In one embodiment, a core comprises or is formed of an inorganic material. In some embodiments, a core comprises or is formed of an organic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide).

In some embodiments, the coating comprises lipids. In some embodiments, the coating comprises pH sensitive lipids. In some embodiments, the pH sensitive lipids comprise octadecylamine-p$(API\text{-}L\text{-}ASP)_{10}$ (pH-ADT). In some embodiments the coating comprises of phospholipids. In some embodiments, the coating comprises 1,2-dipalmitoyl-sn-glycero-3-phosphocholine (DPPC), 1,2-dioleoyl-sn-glycero-3-phosphocholine (DOPC), 1,2-dipalmitoyl-sn-glycero-3-phosphoethanolamine (16:0), 1,2-distearoyl-sn-glycero-3-phosphoethanolamine (18:0 PE), sphingomyelin, 1,2-dioleoyl-3-trimethylammonium-propane (DOTAP), or a combination thereof.

It should be understood that the components described herein, such as the lipids, phospholipids, alkyl groups, polymers, proteins, polypeptides, peptides, enzymes, bioactive agents, nucleic acids, and species for targeting described above (which may be optional), may be associated with a synthetic nanoparticle in any suitable manner and with any suitable portion of the structure, e.g., the liposome/lipid layer, the core, or both. Furthermore, such components can be used, in some embodiments, transport of materials (e.g., proteins, peptides, polypeptides, nucleic acids, nutrients) from one or more components of a subject (e.g., cells, tissues, organs, particles, fluids (e.g., blood), and portions thereof) to a structure described herein, and/or from the structure to the one or more components of the subject. In some cases, the components have chemical and/or physical properties that allow favorable interaction (e.g., binding, adsorption, transport) with the one or more materials from the subject (e.g., cell surface receptors, SR-B1).

Pharmaceutical Compositions

As described herein, the synthetic nanoparticles may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for treating cancer or other andrographolide sensitive disorders and/or diseases associated therewith, or other conditions. It should be understood that any suitable structures described herein can be used in such pharmaceutical compositions, including those described in connection with the figures. In some cases, the structures in a pharmaceutical composition have a nanostructure core comprising an inorganic material and a shell substantially surrounding and attached to the nanostructure core. In some embodiments, the structures in a pharmaceutical composition have a nanostructure core comprising an organic material and a liposome shell substantially surrounding and attached to the nanostructure core.

The pharmaceutical compositions may be specially formulated for administration in solid or liquid form, including those adapted for the following: administration to the respiratory system, including, intra-nasal administration, for example, liquids, sprays, mists, aerosols, or inhalants powders, oral administration, for example, liquids, sprays, mists, aerosols, or inhalants, drenches (aqueous or non-aqueous solutions or suspensions), tablets, e.g., those targeted for buccal, and sublingual, boluses, powders, granules, pastes for application to the tongue; as a sterile solution or suspension, or sustained-release formulation; spray applied to the oral cavity; for example, as cream or foam. In some embodiments, the liquid or solid may be a composition or formulation for use in a nebulizer or other device which transforms the composition or formulation into a form for administration to the respiratory system. In some instances, the composition may be in the form of a solid, which is released in the oral or nasal cavity for release into the respiratory system. In some embodiment, the release may be triggered by contact with the saliva of the cavity, in some embodiments, the release may be triggered by pressure (e.g., applied force by fingers, tissues, teeth, tongue, lips, etc.).

The phrase “pharmaceutically acceptable” is used herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase “pharmaceutically acceptable carrier” as used herein means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be “acceptable” in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Pharmaceutical compositions described herein include those suitable for administration to the respiratory system. The formulations may conveniently be presented in unit dosage form and may be prepared by any methods well known in the art of pharmacy. The amount of active ingredient that can be combined with a carrier material to produce a single dosage form will vary depending upon the host being treated, and the particular mode of administration. The amount of active ingredient that can be combined with a carrier material to produce a single dosage form will generally be that amount of the compound that produces a therapeutic effect. Generally, this amount will range from about 1% to about 99% of active ingredient, from about 5% to about 70%, or from about 10% to about 30%.

The compositions of the present disclosure (e.g., synthetic nanoparticles) suitable for intra-nasal administration may be in the form of liquid, sprays, mists, powders, inhalants, aerosols, granules, or other formulations which facilitate administration to the respiratory system via nasal administration. The compositions of the present disclosure (e.g., synthetic nanoparticles) suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the respiratory system, optionally, in a delayed manner. Examples of embedding compositions that can be used include polymeric substances and waxes. The active ingredient can also be in micro-encapsulated form, if appropriate, with one or more of the above-described excipients.

Liquid dosage forms for administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The active compound may be mixed under sterile conditions with a pharmaceutically acceptable carrier, and with any preservatives, buffers, or propellants, which may be required.

The pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the inventive structures may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some embodiments, the synthetic nanoparticles and/or compositions of the disclosure are administered to a subject systemically. Systemic administration can take place via enteral administration (e.g., absorption of the synthetic nanoparticles and/or compositions of the disclosure through the gastrointestinal tract), absorption of the synthetic nanoparticles and/or compositions of the disclosure through the respiratory system (e.g., inhalation, or any of the administration routes to the respiratory system disclosed herein), or parenteral administration (e.g., injection, infusion, or implantation).

Therapeutically Effective Amount

The term "therapeutically effective amount," as may be used herein, refers to that amount of a material or composition comprising an inventive structure that is effective for producing some desired therapeutic effect in a subject at a reasonable benefit/risk ratio applicable to any medical treatment. Accordingly, a therapeutically effective amount may, for example, prevent, delay, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

An effective amount may depend on the particular condition to be treated. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

As used herein, the term "treating" or "treatment" refers to the application or administration of a synthetic nanoparticle to a subject, who has cancer, a symptom of cancer, or is at risk of cancer, with the purpose to prevent, cure, heal, alleviate, relieve, alter, remedy, ameliorate, improve, or affect the disorder resulting from the disease (e.g., cancer).

In some instances, the synthetic nanoparticle may be administered on demand. For instance, it may be administered to the subject when the subject has been diagnosed with cancer or is at risk of being diagnosed with cancer, or when a subject exhibits symptoms of having cancer. In other instances it may be administered on a regular schedule such as once a day, twice a day, once every other day, once a week, twice a day, or once a day for one week to one month. In some embodiments, it may be administered once every other day, or some other increment (e.g., every second day, every third day, etc.). The synthetic nanoparticle may be mixed with or added to a food or drink product. For instance, it may be in a powder or liquid form that can be added to the food or drink. In some embodiments, it may be in the form of a spray, mist, inhalant, or other vehicle or formulation suitable for oral or intra-nasal administration. Additionally, it may be in a separate dosage form such as a capsule which can be delivered to the subject. The terms "administered" or delivered" are intended to encompass both administration by a health care worker as well as self-administration by a patient (e.g., subject).

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

The present disclosure also provides any of the above-mentioned compositions (e.g., synthetic nanoparticles, compositions thereof) useful for diagnosing, preventing, treating, or managing a disease or bodily condition packaged in kits, optionally including instructions for use of the composition. That is, the kit can include a description of use of the composition for participation in any disease or bodily condition, including those associated with abnormal SR-B1 expression levels. The kits can further include a description of use of the compositions as discussed herein. The kit also can include instructions for use of a combination of two or more compositions described herein. Instructions also may be provided for administering the composition by any suitable technique, such as orally, intravenously, intra-nasally, or via another known route of drug delivery.

The kits described herein may also contain one or more containers, which can contain components such as the structures, signaling entities, and/or biomolecules as described. The kits also may contain instructions for mixing, diluting, and/or administrating the compounds.

The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment. The compositions of the kit may be provided as any suitable form and for any of the administration method known in the art, for example, as liquid solutions, mists, sprays, inhalants, or as dried powders. The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as the secondary diseases or conditions disclosed herein. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition. In some embodiments, a subject may be diagnosed with, or otherwise known to have, a disease or bodily condition associated with cancer, as described herein. In certain embodiments, a subject may be selected for treatment on the basis of a known disease or bodily condition in the subject. In some embodiments, a subject may be selected for treatment on the basis of a suspected disease or bodily condition in the subject. In some embodiments, the composition may be administered to prevent the development of a disease or bodily condition. However, in some embodiments, the presence of an existing disease or bodily condition may be suspected, but not yet identified, and a composition of the invention may be administered to diagnose or prevent further development of the disease or bodily condition.

Any of the compositions disclosed herein (e.g., synthetic nanoparticles) may be administered by any administration route known in the art. For example, in some embodiments, one of ordinary skill in the art of medicine, can administer the agents via conventional routes, e.g., administered orally, parenterally, by inhalation spray, topically, rectally, nasally, buccally, vaginally or via an implanted reservoir. In some embodiments, the synthetic nanoparticles of the disclosure and/or any of the pharmaceutical compositions of the disclosure are formulated into a form for intravenous administration. In some embodiments, the methods of the disclosure comprise administering any of the synthetic nanoparticles of the disclosure and/or any of the pharmaceutical compositions of the disclosure to a subject. In some embodiments, the synthetic nanoparticles of the disclosure and/or any of the pharmaceutical compositions of the disclosure are formulated into a liquid for administration. In some embodiments, the synthetic nanoparticles of the disclosure and/or any of the pharmaceutical compositions of the disclosure are formulated into a spray for administration.

In some embodiments, the synthetic nanoparticles of the disclosure and/or any of the pharmaceutical compositions of the disclosure are formulated into a mist for administration. In some embodiments, the synthetic nanoparticles of the disclosure and/or any of the pharmaceutical compositions of the disclosure are formulated into an inhalant for administration. In some embodiments, the synthetic nanoparticles of the disclosure and/or any of the pharmaceutical compositions of the disclosure are formulated into an aerosol for administration. In some embodiments, the synthetic nanoparticles of the disclosure and/or any of the pharmaceutical compositions of the disclosure are formulated into a powder for administration. In some embodiments, the methods of the disclosure comprise administering any of the synthetic nanoparticles of the disclosure and/or any of the pharmaceutical compositions of the disclosure to a subject topically. In some embodiments, the topical administration is to a tissue. In some embodiments, the topical administration is topically to an internal tissue. In some embodiments, the methods of the disclosure comprise administering any of the synthetic nanoparticles of the disclosure and/or any of the pharmaceutical compositions of the disclosure to a subject by oral administration. In some embodiments, the oral administration facilitates administration topically to an internal tissue. In some embodiments, any of the synthetic nanoparticles of the disclosure and/or any of the pharmaceutical compositions of the disclosure are formulated for topical administration. In some embodiments, any of the synthetic nanoparticles of the disclosure and/or any of the pharmaceutical compositions of the disclosure are formulated for oral administration. In some embodiments, any of the synthetic nanoparticles of the disclosure and/or any of the pharmaceutical compositions of the disclosure are formulated into a liquid. In some embodiments, the liquid is consumed orally. In some embodiments, the liquid is encapsulated. In some embodiments, the liquid is placed into a gel capsule for consumption. In some embodiments, the liquid is in a shell for consumption. In some embodiments, the liquid is in a pill for consumption. In some embodiments, the synthetic nanoparticles of the disclosure and/or any of the pharmaceutical compositions of the disclosure are formulated into a powder. In some embodiments, the powder is consumed by the subject. In some embodiments, the powder is formulated into a pill. In some embodiments, the powder is mixable with a liquid. In some embodiments, the powder is encapsulated.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Applications

As described herein, the methods and compositions of the present invention can be used to treat or prevent several diseases associated with cell surface receptors (e.g., SR-B1) or andrographolide sensitivity. For example, without limitation, cancer, B-cell lymphoma, or T-cell lymphoma. In some embodiments, a subject is identified as having a disorder associated with cell surface receptors (e.g., SR-B1) or andrographolide sensitivity, or as being at risk of or suspected of the same. The status of a subject as having, being at risk of having, or suspected of having such a disease or disorder may be assessed using any routine screening tests known in the art.

In some embodiments, the present disclosure relates to a method of targeting release of a drug having a low water solubility by administering to a subject any of the synthetic nanoparticles as disclosed herein. In some embodiments, the synthetic nanoparticles are applied to target a microenvironment by its pH difference relative to the environment absent a disease or disorder.

In some embodiments, the subject has cancer. In some embodiments, the compositions of the instant disclosure (e.g., synthetic nanoparticle) may be delivered to a cancer cell (e.g., cell may be contacted) in vitro or ex vivo. The subject may have had cancer in the past and is presently in remission. The subject may presently have an active cancer diagnosis (e.g., is not in remission). The subject may have been diagnosed in any means known in the art to receive the status of having cancer. In some embodiments, the cancer is selected from: B-cell lymphoma and T-cell lymphoma. In some embodiments, the cancer is comprised of SR-B1 positive cancer cells. In some embodiments, the cancer is comprised of SR-B1 negative cancer cells. In some embodiments, the drug of the synthetic nanoparticle is a chemotherapeutic agent. In some embodiments, the drug is Andro or derivatives thereof. In some embodiments, the effective amount of the nanoparticle comprises a sub-therapeutic amount of a drug, wherein a subtherapeutic amount comprises an amount that is less than a minimal amount required for producing a therapeutic result in a buffer or alcohol carrier.

In some aspects, the disclosure relates to a method of reducing, in a population of cells, the number of live cancer cells, the method comprising administering an effective amount of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticle is any of the synthetic nanoparticles as described herein.

In some aspects, the disclosure relates to a method of treating a subject who has a stroke or has suffered from a stroke, comprising, administering an effective amount of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticle is any of the synthetic nanoparticles as described herein. In some embodiments, the disease or disorder may be related to a stroke the subject is experiencing or has experienced in the past. In some embodiments, the disease or disorder causes a cell or microenvironment within a subject to have a pH different from the pH the cell or microenvironment would have absent the disease or disorder.

In some embodiments, the nanoparticle is administered to the subject within 1 month of the stroke in the subject. In some embodiments, the nanoparticle is administered to the subject within 1 week of the stroke in the subject. In some embodiments, the nanoparticle is administered to the subject within 1 day of the stroke in the subject. In some embodiments, the nanoparticle is administered to the subject within 12 hours of the stroke in the subject.

In some embodiments, the drug comprises an anti-inflammatory agent. In some embodiments, the drug is selected from the group consisting of anti-platelet drugs, anticoagulants, tissue plasminogen activator, statins, and blood pressure drugs.

In some aspects, the disclosure relates to a method for modulating an immune response in a subject, comprising, administering an effective amount to modulate an immune response of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticle is any of the synthetic nanoparticles as described herein.

In some embodiments, the synthetic nanoparticle enhances cytotoxic T cells, natural killer (NK) cells, phagocytosis, antibody-dependent cell-mediated cytotoxicity (ADCC), or a combination thereof.

In some aspects, the disclosure relates to a method of inhibiting viral activity in a subject, comprising, administering an effective amount to inhibit viral activity of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticle is any of the synthetic nanoparticles as described herein.

In some embodiments, the synthetic nanoparticle enhances cytotoxic T cells, natural killer (NK) cells, phagocytosis, antibody-dependent cell-mediated cytotoxicity (ADCC), or a combination thereof.

In some embodiments, the subject has been infected by, or is at risk of being infected by, influenza A virus, hepatitis B virus, hepatitis C virus, Herpes simplex 1 virus, Epstein-Barr virus, human papilloma virus, human immunodeficiency virus, and/or Chikungunya virus.

In some aspects, the disclosure relates to a method increasing macrophage activity in a subject, comprising, administering an effective amount to inhibit viral activity of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome. In some embodiments, the synthetic nanoparticle is any of the synthetic nanoparticles as described herein.

In some embodiments, the subject is administered, or the cell is contacted by, any of the compositions described herein (e.g., synthetic nanoparticles). The compositions disclosed herein may be administered by any administration route known in the art. For example, in some embodiments, one of ordinary skill in the art, may administer a composition via conventional routes, e.g., administered orally, parenterally, by inhalation spray, topically, rectally, nasally, buccally, vaginally or via an implanted reservoir.

In some embodiments, the subject is administered, or a cell contacted by, a composition (e.g., synthetic nanoparticle) at least once. In some embodiments, a subject receives multiple administrations, or a cell is contacted multiple times. For example, without limitation, the subject may receive at least 2 administrations, or a cell contacted at least 2 times (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more). In some embodiments, the administrations or contacts are irregularly spaced (e.g., not an equal duration of time between administrations or contacts). In some embodiments, the administrations or contacts are equally spaced (e.g., an equal duration of time between administrations or contacts). In some embodiments, the subject receives, or the cell is contacted, at least one administration per month. In some embodiments, the subject receives, or the cell is contacted, at least one administration per week. In some embodiments, the subject receives, or the cell is contacted, at least one administration per day. In some embodiments, the subject receives, or the cell is contacted, at least two administrations per day. In some embodiments, where there is more than one administration or contact, the administrations or contacts are of the same route. In some embodiments, where there is more than one administration or contact, the administrations or contacts are of different routes.

EXAMPLES

Introduction

In this study, pH-sensitive liposomal formulation carrying a low water soluble drug and a targeting moiety that is an apolipoprotein was developed. The synthetic nanostructure was demonstrated to be useful as an anti-cancer agent using in vitro studies on various lymphoma including B cell lines, T cell lines, and CLL patient lymphoma cells.

Experimental Conditions

Materials

The lipids egg-phosphatidylcholine, lipids egg-phosphatidylcholine (EPC), 1,2-distearoyl-sn-glycero-3-phosphoethanolamine-N-[methoxy (polyethylene glycol)-2000] (DSPE-PEG2000), and DSPE-PEG-Cy 5 were purchased from Avanti Polar Lipids Inc. (Alabaster, AL, USA). Lysotracker Green DND-26 and ProLong™ Gold Antifade Mountant with DAPI were purchased from ThermoFisher scientific (Waltham, MA, USA). Andrographolide was purchased from Sigma-Aldrich (St. Louis, MO, US). Apo-A1 was purchased from Meridian Life Sciences (Memphis, Tennessee, US). All other chemicals used were analytical grade.

Methods

Synthesis of pH-Sensitive Lipid pH-sensitive lipid (pH-L) was synthesized based on a previously reported procedure (See, Park, W., et al., Acidic pH-triggered drug-eluting nanocomposites for magnetic resonance imaging-monitored intra-arterial drug delivery to hepatocellular carcinoma. ACS applied materials & interfaces, 2016. 8(20): p. 12711-12719). Octadecylamine (0.3 g 1.2 mmol) was dissolved in a mixture of N,N-dimethylformamide (DMF, 10 mL) and $CH_2Cl_2$ (50 mL) and then stirred at room temperature for 2 hours (h). As-synthesized β-Benzyl-1-aspartate N-carboxy anhydride (BLA-NCA, 3 g, 12 mmol) was dissolved in DMF (10 mL) and dropped into the octadecylamine solution. The reaction mixture was stirred for 2 days. To remove $CH_2Cl_2$, the reaction solution was concentrated in a rotary evaporator for 30 min under vacuum. The final product was precipitated in diethyl ether (200 mL) and collected by centrifugation (3500 rpm) for 5 min. This process repeated three times to remove any unreacted impurity. The precipitate was dried under vacuum at room temperature. Finally, pH-sensitive lipid [octadecylamine-p(API-Asp)$_{10}$] was synthesized via aminolysis of the octadecylamine-polyBLA with 1-(3-aminopropyl) imidazole (API). As-synthesized octadecylamine-p(BLA)$_{10}$ (0.2 g, 74.8 μmol) was dissolved in DMF (5 mL). API (1 g, 7.9 mmol) was added to the octadecylamine-p(BLA)$_{10}$ solution, which was stirred for 12 h at room temperature. After 12 h, the reaction mixture was added dropwise into a cooled aqueous solution of 0.1 N HCl (20 mL) to neutralize the reaction mixture. To remove any impurity, the solution was dialyzed by use of a cellulose membrane (molecular weight cutoff (MWCO) 1000, Spectrum Laboratories, Rancho Dominguez, CA) against 0.01 N HCl solution three times.

Preparation of Apo-A1-Coated pH-Sensitive Liposomes (pH-ALs)

Apo-A1-coated pH-sensitive liposomes were prepared using the film hydration technique. Briefly, the lipids, egg-phosphatidylcholine (EPC, 20 mg):1,2-distearoyl-sn-glycero-3-phosphoethanolamine-N-[methoxy (polyethylene glycol)-2000] (DSPE-PEG2000, 6 mg), in a molar ratio of 6.5:0.5, were dissolved in a solution of chloroform. pH-sensitive lipid (4 mg) and Andro (1.5 mg, 3 mg, and 6 mg, respectively) dissolved in methanol was added to the prepared lipids solution. The solvent was evaporated using a rotary evaporator (Büchi-R144, Switzerland) at 65° C. to obtain a lipid film, which was further dried under vacuum. The film was hydrated with a solution of Apo-A1 (3 mg) in 10 mM HEPES buffer.

Characterization of pH-ALs

The effective hydrodynamic diameter ($D_{eff}$) and zeta potentials of liposomes were measured by photon correlation spectroscopy using a Zetasizer Nano-ZS (Malvern Instruments, UK), equipped with the Multi Angle Sizing Option (BI-MAS). Liposomes at different pH conditions (0.01 wt %) were prepared by 10-fold dilution of the stock solution using PBS solution (pH 6.0-7.4) separately. Before the measurements, the liposome solutions were incubated at room temperature for 3 h (n=3). The software provided by the manufacturer was used to calculate the $D_{eff}$, and zeta potential values; average values for each parameter were calculated from three measurements of each sample (n=3). The drug-loading content and efficiency were calculated using the following equations:

Drug-loading content (%)=(weight of loaded Andro in liposomes)/(weight of total Andro loaded liposomes)×100.

Drug-loading efficiency (%)=(weight of loaded Andro in liposomes)/(weight of Andro initially added to formulations)×100.

Drug Release

For drug release testing, pH-ALs containing 200 μg of Andro were dispersed in 1 ml of PBS at different pH values (pH 7.4 and 6.5). The mixtures were transferred to a Spectra/Por dialysis membrane tube with a molecular weight cut-off of 6000-8000. Each membrane tube was immersed in a vial containing 50 ml of PBS solution adjusted to a different pH (pH 7.4 and 6.5). The release of Andro from the pH-ALs was tested under mechanical shaking (100 rpm) at 37° C. At predetermined time intervals, herein 1, 2, 4, 8, 12, and 24 hours, the outer phase of the dialysis membrane was withdrawn for drug concentration analysis and replaced with the same amount of fresh medium to maintain a sink condition.

Cell Culture

B cell lymphoma cell lines (Jeko, SUDHL4, and U2932) and T cell lymphoma cell line (Hut78 and Jurkat) were purchased from ATCC (VA, USA). The lymphoma cell lines were cultured in RPMI-1640 medium with L-glutamine and 10% FBS in the presence of 1% penicillin/streptomycin (Invitrogen, CA, USA). Suspended cells were cultured in T75 flasks and incubated at 37° C. and 5% CO2.

CLL Patient Lymphocyte Isolation

After written consent was approved by the Northwestern University Institutional Review Board, peripheral blood was drawn from a healthy volunteer in Li-Heparin-coated tubes. Fresh (<4 h post-donation) whole human blood was diluted 1:1 with RPMI medium. To a 50-mL tube, 10 mL Ficoll Hystopaque and 20 mL diluted blood were added. Samples were centrifuged (~480×g, 20 min, room temperature), and the supernatant was removed. The lymphocytes, which appeared as a milky white layer, were transferred to a new tube, diluted to 50 mL with fresh RPMI, and centrifuged (~500×g, 6 min). The wash step was repeated two times, and the final pellet was resuspended in 5 mL growth medium (RPMI 1640 with L-glutamine, 10% FBS, and 1% penicillin/streptomycin; Invitrogen). If necessary, red blood cells were removed by adding 10 mL cold red blood cell lysis buffer to the lymphocyte pellet. After sitting 10 min on ice, the sample was washed two times with RPMI. Then, the final pellet was resuspended in growth medium at $1\times10^6$ cells/mL.

Endosome Disruption by the Confocal Microscopy

Endosome disruption in cancer cells induced by pH sensitive liposome (pH-ALs) were observed by confocal microscopy (A1R spectral, Nikon, Japan). DSPE-PEG-Cy 5 was utilized to prepare the pH-ALs instead of DSPE-PEG. Jeko cells were incubated with Cy 5 labelled pH-ALs, Lysotracker Green DND-26, and DAPI for 60 mins. After the incubation, cells were collected by the centrifugation (500 g for 5 min). Subsequently, the concentrated cells after washing on Glass Bottom Dishes (MatTek corp., MA, US) were washed three times with cold DPBS. Intracellular alteration in Jeko cells were observed by confocal microscopy (A1R spectral, Nikon, Japan).

Cell Viability by MTS Assay

The effects of liposome-andrographolide on cell viability was measured by MTS assay in different cell lines according to the instructions of an improved detection kit provided by the manufacturer (The CellTiter 96 AQueous One Solution Cell Proliferation Assay, Promega). Briefly, $2.5\times10^4$ cells/90 μl were seeded in 96 well micro titer plates. After incubating with different concentrations of Andro (10 μl) for the designated times, 20 μL MTS solution was added to each well and the plates were incubated for an additional 1-4 h at 37° C. The absorbance was read at 490 nm using a micro plate reader (MRX Revelation) (DYNEX Technologies, Chantilly, VA). The OD values were expressed as % over the control group. Since reduction of MTS can only occur in metabolically active cells the level of activity is a measure of the viability of the cells.

Apoptosis Analysis

After incubations and washing, $1\times10^6$ cells were labeled with Annexin V-FITC and PI reagent in the binding buffer according to the Annexin V-FITC apoptosis detection kit instruction provided by the manufacturer (Invitrogen). The Fluorescent signals of FITC and PI were detected respectively at 518 nm and 620 nm on a Beckman coulter FACS machine (Beckman, CA, USA). For each analysis 30,000 events were recorded. Results were analyzed and calculated by FCS Express V3 software (De Novo Software, Canada) and Excel (Microsoft). The % apoptosis was the sum of cells with early apoptosis (Annexin V-FITC$^+$/PI$^-$) and late apoptosis (Annexin V-FITC$^+$/PI$^+$).

Statistics

Data are expressed as the mean±SD unless otherwise noted. Comparisons between two values were performed using an unpaired Student t-test. For multiple comparisons among different groups of data, the significant differences were determined by the Bonferroni method. Significance was defined as $P\leq0.05$.

Results and Discussion pH sensitivity of the lipid, pH-L is evident in that it has a clear difference at pH 7.4 and 6.5. pH sensitivity of pH-L was confirmed by chemical structure of pH-L, structural analysis by 1H-NMR, and confirmed by transmittance at determined pH conditions and by pH cyclization. Since the protonation of imidazole moiety of pH-L at acidic pH conditions increased the hydrophilicity by the positive changes, pH-L showed low transmittance at 7.4 and 6.5.

Physicochemical Properties of pH-Sensitive Lipid (pH-L)

The pH-sensitivity of liposomes (pH-ALs) was confirmed clearly by using DLS at different pH conditions (FIG. 1*a* and Table 1). At pH 7.4, pH-ALs were nano-sized particles with a size of c.a. 200 nm in diameter and had a narrow size distribution. pH-ALs showed a positive charge due to the protonated imidazole groups at pH 6.5, while they exhibited a negative charge at pH 7.4 (FIG. 1*b*). Since the protonation of imidazole groups could induce the electric repulsion among positive charges, pH-ALs showed a structural change with bimodal size distribution at pH 6.5.

To optimize the drug (i.e, Andro) loading into the liposome, the concentration of Andro depending on target content (5, 10, and 20%) was analyzed by the absorbance at 225 nm (Table 1). The loading capacity of liposomes for Andro is about 9.2%, based on the loading efficiency. Therefore, a liposomal formulation of about 10% would be the most efficient for the loading of Andro into liposomes. Based on the physicochemical properties including loading profile, particle size, and zeta potential, following studies were performed using 10% targeting pH sensitive liposome (pH-AL).

Drug Release

Figure 2A:
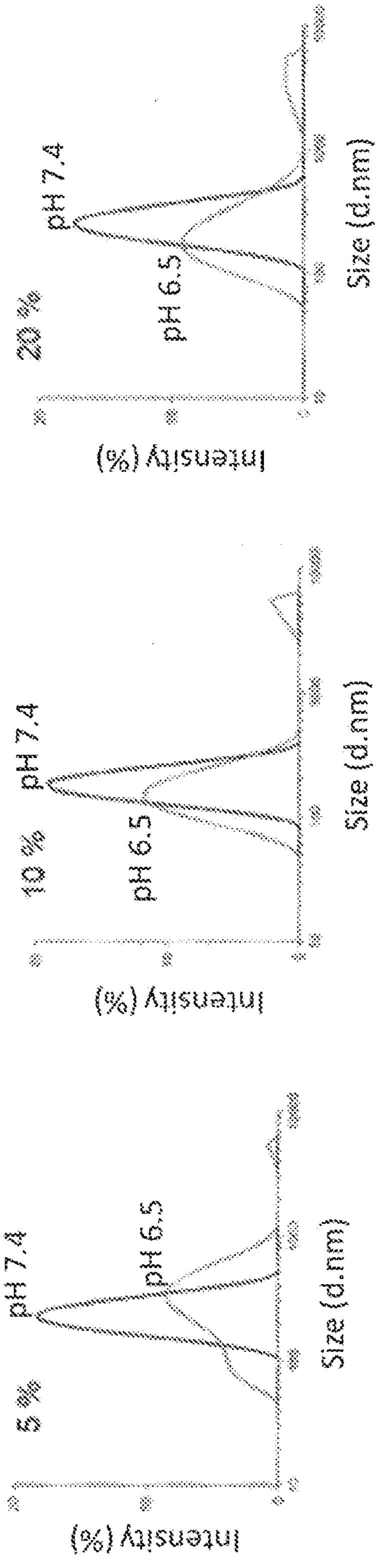
FIGS. 2A-2B show characterizations of pH-ALs (pH-ALs are also known as Apolipoprotein coated pH sensitive liposomes herein (e.g., synthetic nanoparticles)).

To investigate the drug release profile, pH-ALs were exposed to different pH conditions (pH 7.4 and 6.5) (FIG. 2*a*). At pH 7.4, drug release profiles from the liposome similarly showed less than ca. 50% maximum cumulative release over 24 hours. In contrast, pH 6.5 led to a drastic increase of Andrographolide (Andro) release from pH-ALs. This might be attributed to altered ionization of imidazolium in the P(Asp-g-Im) block to form the liposome depending upon pH. At pH levels above 7.4, pH-ALs formed stable liposomes incorporating pH-L including hydrophobic P(Asp-g-Im) block. They could also incorporate hydrophobic Andro through stacking and hydrophobic interactions, inhibiting the release of Andro. Protonation of imidazole of pH-L could destabilize the liposome at pH 7.0, and Andro could be released from pH-L.

Endosome Disruption by the Confocal Microscopy

Figure 2B:
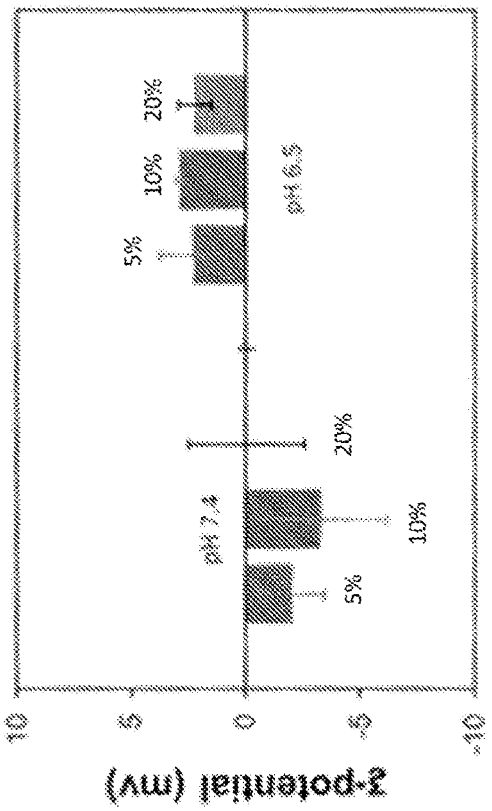
Figure 3A:
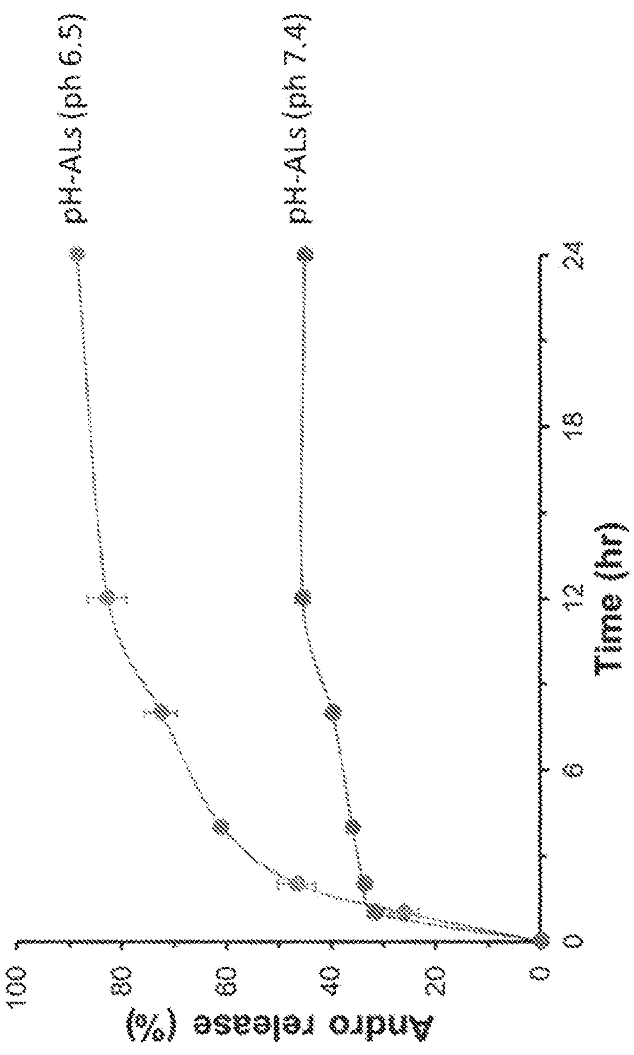
FIGS. 3A-3B show an in vitro study of pH-ALs.
Figure 3B:
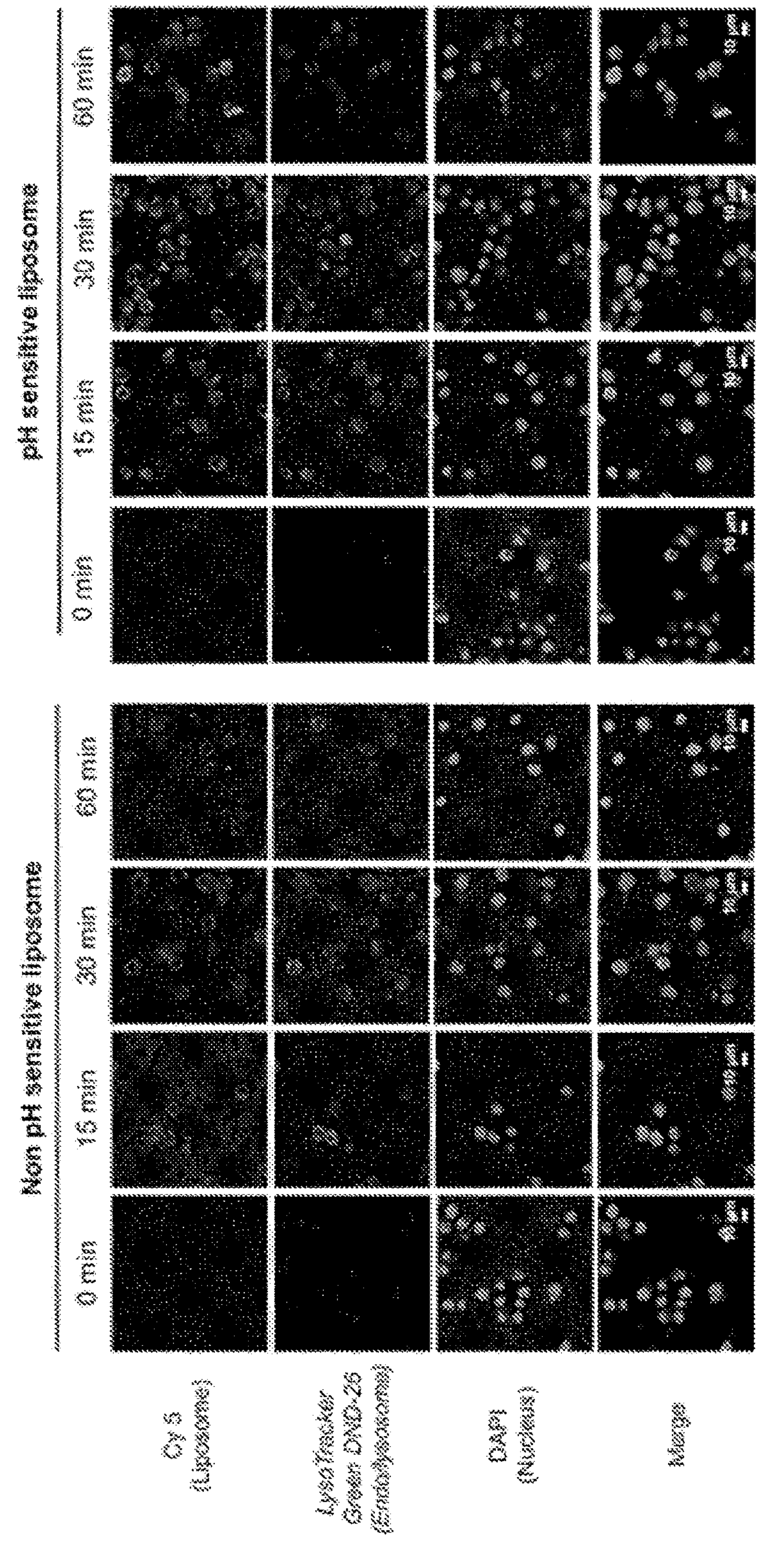
Figure 4A:
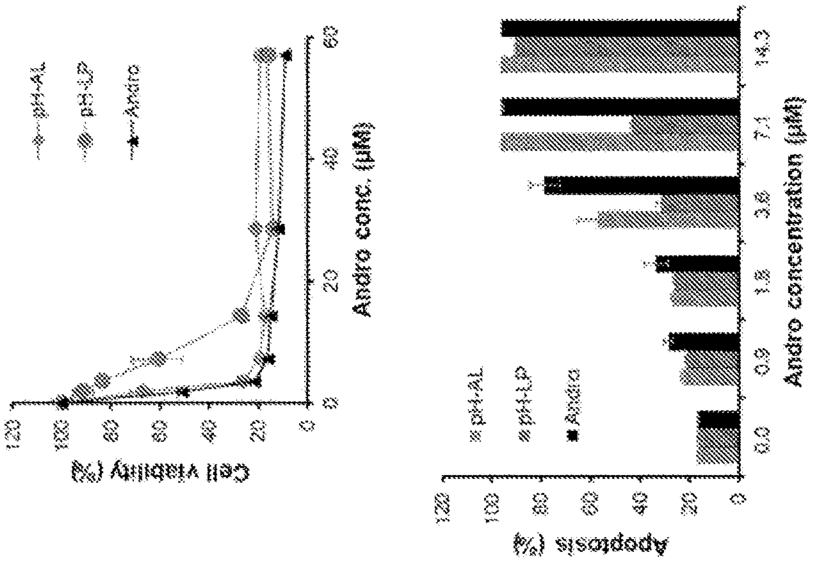
FIGS. 4A-4C show cytotoxicity (top panels of FIGS. 4A-4C) and apoptosis (bottom panels of FIGS. 4A-4C) of B-cell lymphoma cell lines: Jeko (FIG. 4A); SUDHL4 cells (FIG. 4B); and U2932 (FIG. 4C) treated by Andro, pH sensitive liposomes without Andro (pH-LP), and pH sensitive liposomes with Andro (pH-AL) after 72 hour incubation.
Figure 4B:
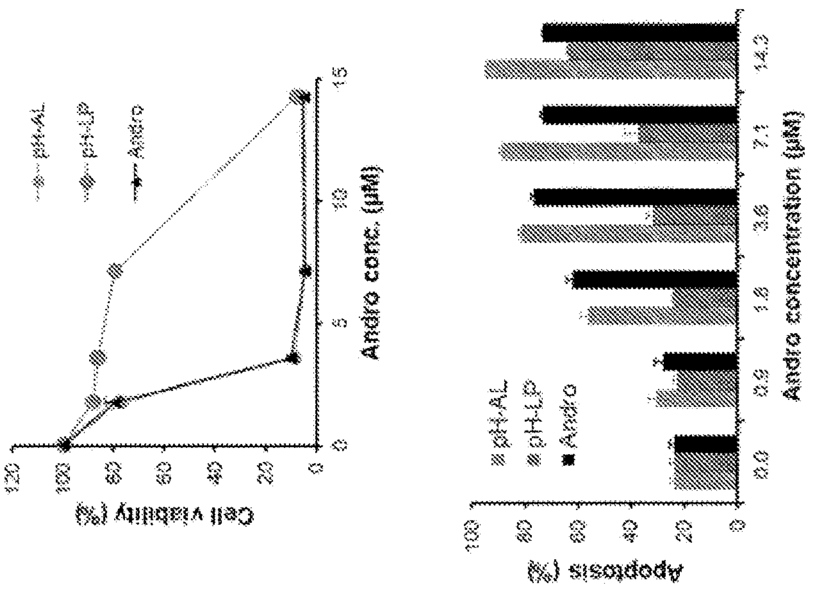
Figure 4C:
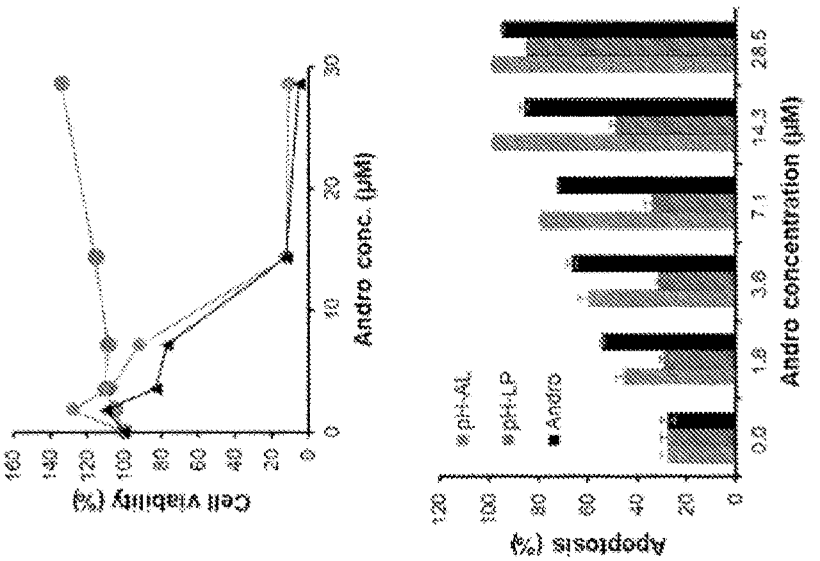
Figure 5A:
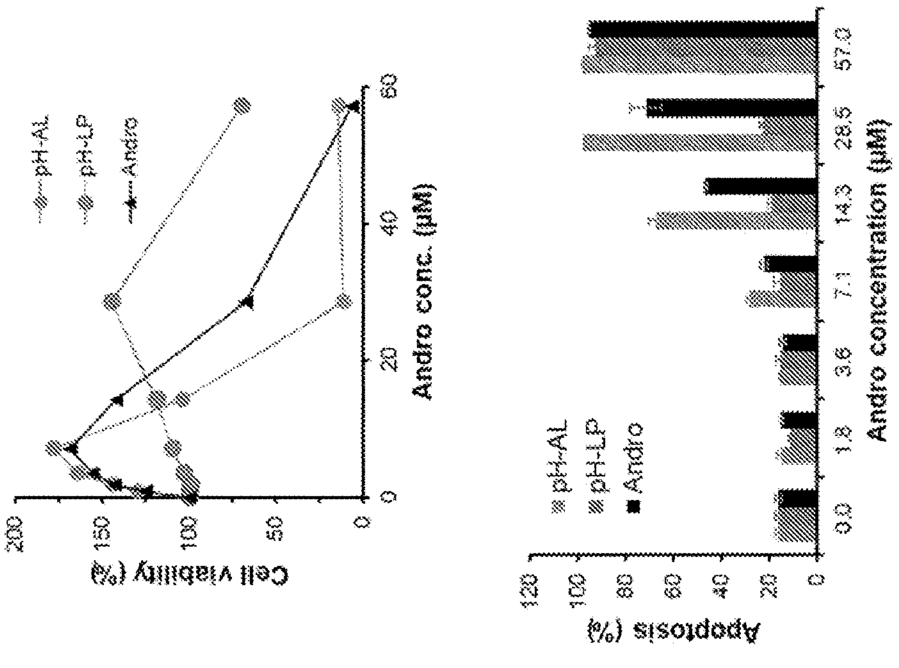
FIGS. 5A-5B show cytotoxicity (top panels of FIGS. 5A-5B) and apoptosis (bottom panels of FIGS. 5A-5B) of a T-cell lymphoma cell line. Hut-78 cell (FIG. 5A) and Jurkat cells (FIG. 5B) by MTS assay and flow cytometry treated by Andro, pH-LP (also referred to herein as pH sensitive lipids (e.g., pH sensitive liposome)), and pH-AL after 72 hour incubation.
Figure 5B:
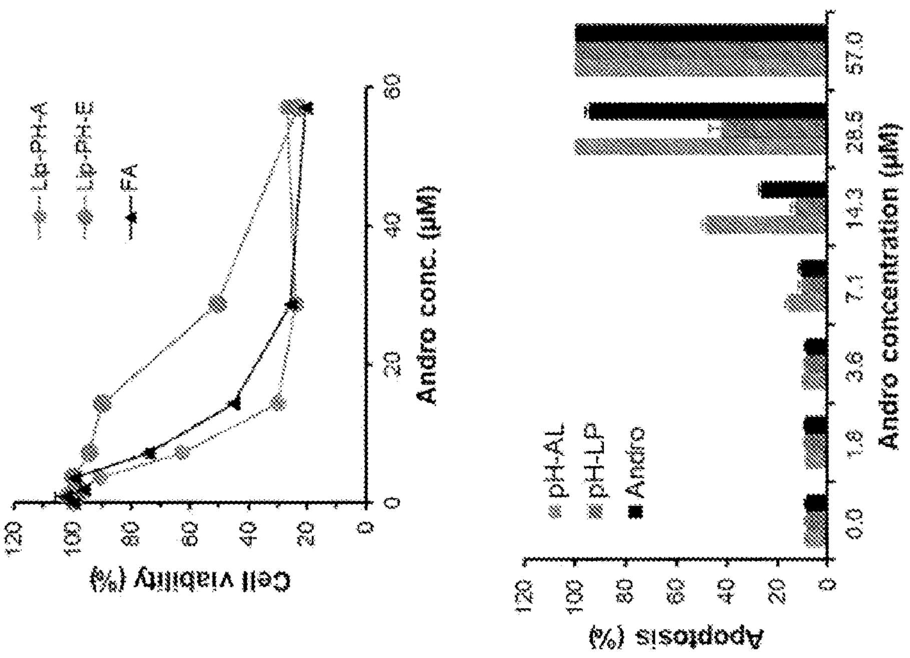
Figure 6:
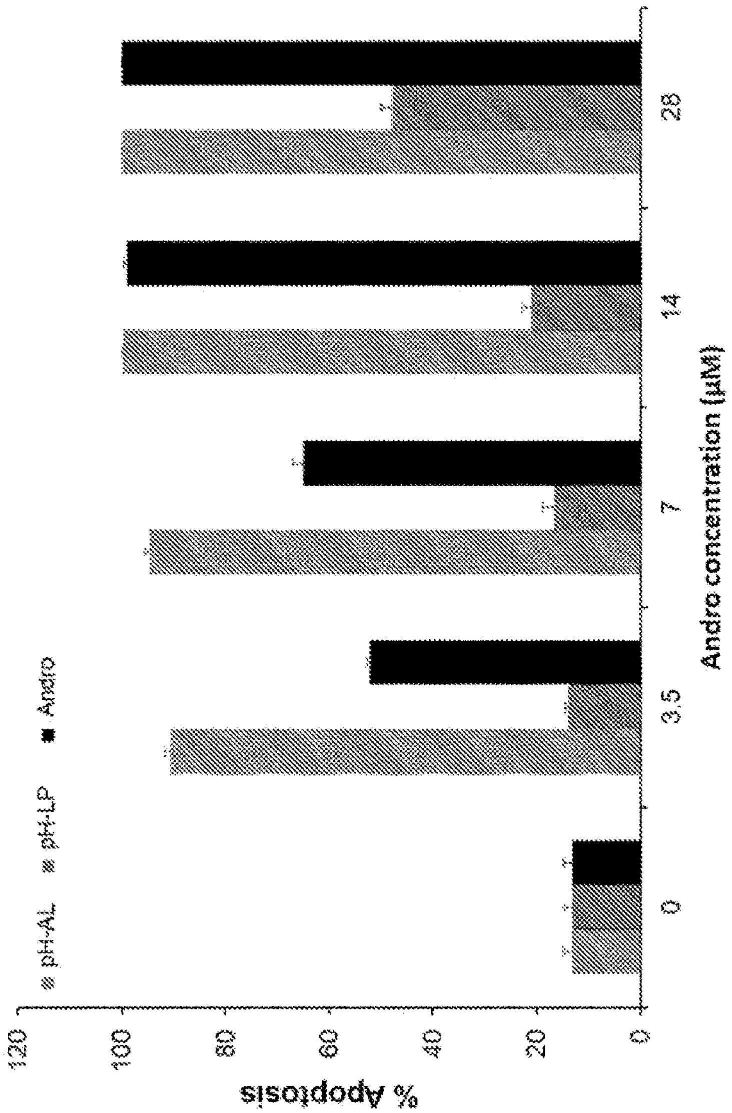
FIG. 6 shows apoptosis on a chronic lymphocytic leukemia patient (CLL) cell line after 18 hours from the treatment.

Confocal imaging of Jeko cells indicated the successful cellular uptake of Andro. Visualizing endosomal disruption by the pH-sensitive nanocarrier, the endosomal compartment was observed by confocal microscopy using different fluorescent dyes, DAPI, Cy 5 labelled liposome and lysotracker Green DND-26. LysoTracker® Green DND-26 showed green fluorescence accumulated in the endosomes and lysosomes inside cells (FIG. 2*b*). LysoTracker and Cy5.5 signals distributed inside cells confirmed the disruption of endolysosomal compartments by a 'proton sponge effect'. During 15-30 min, pH sensitive liposome (pH-AL) showed higher intracellular distribution at the cytoplasm through rupture of endolysosomal compartments by the protonation of imidazole groups on pH-L. Since anionic lipids are located on the plasma and endosomal membranes, positively charged pH-L by protonation of imidazole groups at pH 6.5 could fuse and destabilize the membranes by a 'proton sponge effect' during the endocytosis. At 60 min, pH-sensitive liposomes showed broad intracellular distribution of pH sensitive liposomes compared to the non-pH sensitive liposome with a less aggregated endolysosomal compartment. Liposomes could be fused on the cancer cell membrane by the interaction between Apo-A1 and SR-B1. Therefore, pH-AL was expected to exert a high cytotoxic response against lymphoma as a result of pH dependent Andro release, i.e. by the endosome escape.

Anti-Cancer Effect of pH-ALs Against B-Cell and T-Cell Lymphoma

In order to verify the efficacy of pH-ALs, cytotoxicity and apoptosis of various lymphoma cell lines, including CLL patient samples, were confirmed by MTS assay and FITC Annexin V/PI double staining. Compared to control empty pH sensitive liposomes (pH-LP), pH-AL exerted an improved cytotoxicity (Table 2). Although $IC_{50}$ values of pH-ALs were similar to Andro in B cell lymphoma, ph-ALs showed a distinct improvement considering that Andro had been dissolved into Ethanol. pH-LP showed lower cytotoxicity against B cell lymphoma than the other groups.

The cytotoxicity against T cell lymphoma cell lines including Hut 78 and Jurkat proved the therapeutic benefit of pH-ALs. Due to the endosomal escape, pH-ALs showed higher toxicity than Andro solubilized in Ethanol. Due to the absence of SR B-1, Jurkat was expected to show lower cytotoxicity. Interestingly, Jurkat cells showed lower $IC_{50}$ (13.5 μM) than Hut 78 cells (64.0 μM). The results demonstrate that the endosomal fusion and escape of Andro by the pH-sensitive liposome would be the key factor to improve the cytotoxicity against Lymphoma due to the controlled drug release and endosomal disruption by the protonation of imidazole groups on pH-L, and confirm that the receptor is not necessary.

Anti-Cancer Effect of pH-ALs Against CLL Patient Cell Lines

The apoptosis of a CLL patient (Chronic Lymphocytic Leukemia) cell line was studied to confirm the feasibility as a clinical approach of pH-ALs. Compared to Andro dissolved in ethanol, pH-AL induced significant apoptosis in the range of low concentrations (3.5 and 7 μM). pH-LP possessing Apo-A1 could induce the apoptosis at high concentration.

Overall, andrographolide loaded pH sensitive liposome (pH-ALs) coated with Apo-A1 (pH-ALs) showed high cytotoxicity induced by high apoptosis in not only B cells but also other lymphoma cells including T cell lymphoma and CLL patient cell lines. It is assumed that Andro loaded in ph-ALs could be more effective than Andro itself, because of the pH-sensitive drug release at intracellular compartment (Scheme 1).

Conclusion pH sensitive-Apolipoprotein A1 (Apo A1) based nanoparticles carrying drugs, such as Andro, showed anti-cancer therapeutic effects through a novel mechanism which led to enhanced anti-cancer effects even at lower dosages and against cell lines that do not express the SR-B1 receptor. Thus, the Apo A1 particle could enhance the cellular uptake by targeting SR-B1 and the interaction could induce the scavenger effect. In addition, the particles can utilize a different mechanism, endosomal disruption due to the pH sensitive lipid, resulting in Andro release at the intracellular compartment. The combination of these may provide even further enhancements to the therapeutic effect. Therefore, the novel liposomal formulation could enable anti-cancer therapy with high specificity without severe side effects associated with conventional chemotherapy. The liposomal formulation represent new approaches for lymphoma therapy and other approached disclosed herein.

REFERENCES

1. Armitage, J. O., et al., Non-hodgkin lymphoma. The Lancet, 2017. 390(10091): p. 298-310.
2. Schmitz, R., et al., Genetics and pathogenesis of diffuse large B-cell lymphoma. New England journal of medicine, 2018. 378(15): p. 1396-1407.
3. Ku, E. B., et al., Mitochondria-selective photodynamic tumor therapy using globular PEG nanoparticles. Macromolecular Research, 2016. 24(7): p. 634-639.
4. Yang, S., et al., Biomimetic, synthetic HDL nanostructures for lymphoma. Proceedings of the National Academy of Sciences, 2013. 110(7): p. 2511-2516.

5. Mooberry, L. K., et al., Targeting the SR-B1 receptor as a gateway for cancer therapy and imaging. Frontiers in pharmacology, 2016. 7: p. 466.
6. Yang, S., et al., Biomimetic, synthetic HDL nanostructures for lymphoma. Proc Natl Acad Sci USA, 2013. 110(7): p. 2511-6.
7. Singh, A., et al., Biomimetic Magnetic Nanostructures: A Theranostic Platform Targeting Lipid Metabolism and Immune Response in Lymphoma. ACS Nano, 2019. 13(9): p. 10301-10311.
8. Shen, W. J., S. Azhar, and F. B. Kraemer, SR-B1: A Unique Multifunctional Receptor for Cholesterol Influx and Efflux. Annu Rev Physiol, 2018. 80: p. 95-116.
9. Chen, M., C. Xie, and L. Liu, Solubility of andrographolide in various solvents from (288.2 to 323.2) K. Journal of Chemical & Engineering Data, 2010. 55(11): p. 5297-5298.
10. Meng, W., et al., Stability of active ingredients of traditional Chinese medicine (TCM). Natural product communications, 2009. 4(12): p. 1934578X0900401229.
11. Piazzini, V., et al., Stealth and cationic nanoliposomes as drug delivery systems to increase andrographolide BBB permeability. Pharmaceutics, 2018. 10(3): p. 128.
12. Bulbake, U., et al., Liposomal formulations in clinical use: an updated review.
Pharmaceutics, 2017. 9(2): p. 12.
13. Zylberberg, C. and S. Matosevic, Pharmaceutical liposomal drug delivery: a review of new delivery systems and a look at the regulatory landscape. Drug Delivery, 2016. 23(9): p. 3319-3329.
14. Lamichhane, N., et al., Liposomes: clinical applications and potential for image-guided drug delivery. Molecules, 2018. 23(2): p. 288.
15. Ling, D., et al., Multifunctional tumor pH-sensitive self-assembled nanoparticles for bimodal imaging and treatment of resistant heterogeneous tumors. J Am Chem Soc, 2014. 136(15): p. 5647-55.
16. Qin, Y., et al., Near-infrared light remote-controlled intracellular anti-cancer drug delivery using thermo/pH sensitive nanovehicle. Acta biomaterialia, 2015. 17: p. 201-209.
17. Ma, Y., X. Fan, and L. Li, pH-sensitive polymeric micelles formed by doxorubicin conjugated prodrugs for co-delivery of doxorubicin and paclitaxel. Carbohydrate polymers, 2016. 137: p. 19-29.
18. Zhang, J., et al., pH-sensitive polymeric nanoparticles for co-delivery of doxorubicin and curcumin to treat cancer via enhanced pro-apoptotic and anti-angiogenic activities. Acta biomaterialia, 2017. 58: p. 349-364.
19. Yang, M., et al., pH-sensitive liposomes for intracellular and tumour targeted drug delivery. Liposomes: historical, clinical and molecular perspectives, 2017.
20. Kanamala, M., et al., Mechanisms and biomaterials in pH-responsive tumour targeted drug delivery: a review. Biomaterials, 2016. 85: p. 152-167.
21. Paliwal, S. R., R. Paliwal, and S. P. Vyas, A review of mechanistic insight and application of pH-sensitive liposomes in drug delivery. Drug delivery, 2015. 22(3): p. 231-242.
22. Lim, C., et al., Co-delivery of D-(KLAKLAK) 2 Peptide and Chlorin e6 using a Liposomal Complex for Synergistic Cancer Therapy. Pharmaceutics, 2019. 11(6): p. 293.
23. Gerasimov, O. V., et al., Cytosolic drug delivery using pH- and light-sensitive liposomes. Advanced drug delivery reviews, 1999. 38(3): p. 317-338.
24. Wang, C. Y. and L. Huang, Polyhistidine mediates an acid-dependent fusion of negatively charged liposomes. Biochemistry, 1984. 23(19): p. 4409-4416.
25. Mével, M., et al., Novel neutral imidazole-lipophosphoramides for transfection assays. Chemical communications, 2008(27): p. 3124-3126.
26. Budker, V., et al., pH-sensitive, cationic liposomes: a new synthetic virus-like vector. Nature biotechnology, 1996. 14(6): p. 760-764.
27. Kim, D., et al., Doxorubicin loaded pH-sensitive micelle: antitumoral efficacy against ovarian A2780/DOXR tumor. Pharm Res, 2008. 25(9): p. 2074-82.
28. Kim, G. M., Y. H. Bae, and W. H. Jo, pH-induced micelle formation of poly(histidine-co-phenylalanine)-block-poly (ethylene glycol) in aqueous media. Macromol Biosci, 2005. 5(11): p. 1118-24.
29. Liu, R., et al., Effects of pH-sensitive chain length on release of doxorubicin from mPEG-b-PH-b-PLLA nanoparticles. Int J Nanomedicine, 2012. 7: p. 4433-46.
30. Wu, H., L. Zhu, and V. P. Torchilin, pH-sensitive poly (histidine)-PEG/DSPE-PEG co-polymer micelles for cytosolic drug delivery. Biomaterials, 2013. 34(4): p. 1213-1222.
31. Sim, T., et al., Synergistic photodynamic therapeutic effect of indole-3-acetic acid using a pH sensitive nanocarrier based on poly (aspartic acid-graft-imidazole)-poly (ethylene glycol). Journal of Materials Chemistry B, 2017. 5(43): p. 8498-8505.
32. Park, W., et al., Acidic pH-triggered drug-eluting nanocomposites for magnetic resonance imaging-monitored intra-arterial drug delivery to hepatocellular carcinoma. ACS applied materials & interfaces, 2016. 8(20): p. 12711-12719.
33. Lee, E. S., et al., A feasibility study of a pH sensitive nanomedicine using doxorubicin loaded poly (aspartic acid-graft-imidazole)-block-poly (ethylene glycol) micelles. Journal of Materials Chemistry B, 2014. 2(9): p. 1152-1159.
34. Ling, D., et al., pH-sensitive nanoformulated triptolide as a targeted therapeutic strategy for hepatocellular carcinoma. ACS nano, 2014. 8(8): p. 8027-8039.
35. Moku, G., et al., Delivering anti-cancer drugs with endosomal pH-sensitive anti-cancer liposomes. Biomaterials science, 2016. 4(4): p. 627-638.
36. Mével, M., et al., Important role of phosphoramido linkage in imidazole-based dioleyl helper lipids for liposome stability and primary cell transfection. The journal of gene medicine, 2016. 18(1-3): p. 3-15.
37. Oku, N., et al., Low pH induced membrane fusion of lipid vesicles containing proton-sensitive polymer. Biochemistry, 1987. 26(25): p. 8145-8150.
38. Jones, R. A., et al., Poly (2-alkylacrylic acid) polymers deliver molecules to the cytosol by pH-sensitive disruption of endosomal vesicles. Biochemical Journal, 2003. 372(1): p. 65-75.
39. Faraji, A. H. and P. Wipf, Nanoparticles in cellular drug delivery. Bioorganic & Medicinal Chemistry, 2009. 17(8): p. 2950-2962.

OTHER EMBODIMENTS

Embodiment 1. A synthetic nanoparticle comprising: (a) a pH sensitive liposome comprising a lipid layer comprising at least one pH sensitive lipid; (b) an apolipoprotein in contact with the lipid layer; and (c) a drug having a low water solubility encapsulated within the liposome.

Embodiment 2. The synthetic nanoparticle of embodiment 1, wherein apolipoprotein is apolipoprotein A-I (Apo-A1), apolipoprotein A-II, or apolipoprotein E.

Embodiment 3. The synthetic nanoparticle of any one of embodiments 1-2, wherein the pH sensitive liposome comprises a pH sensitive phospholipid.

Embodiment 4. The synthetic nanoparticle of any one of embodiments 1-3, wherein the pH sensitive liposome comprises octadecylamine-p(API-L-ASP)10 (pH-ADT).

Embodiment 5. The synthetic nanoparticle of any one of embodiments 1-4, wherein the pH sensitive liposome further comprises egg-phosphatidylcholine, lipids egg-phosphatidylcholine (EPC), 1,2-distearoyl-sn-glycero-3-phosphoethanolamine-N-[methoxy (polyethylene glycol)-2000] (DSPE-PEG2000), DSPE-PEG-Cy 5, and/or a combination thereof.

Embodiment 6. The synthetic nanoparticle of any one of embodiments 1-5, wherein the synthetic nanoparticle has a largest cross-sectional dimension of less than or equal to 1000 nanometers (nm).

Embodiment 7. The synthetic nanoparticle of any one of embodiments 1-6, wherein the synthetic nanoparticle has a largest cross-sectional dimension of less than or equal to 500 nanometers (nm).

Embodiment 8. The synthetic nanoparticle of any one of embodiments 1-7, wherein the synthetic nanoparticle has a largest cross-sectional dimension of less than or equal to 200 nanometers (nm).

Embodiment 9. The synthetic nanoparticle of any one of embodiments 1-8, wherein the drug is andrographolide and/or derivative thereof.

Embodiment 10. The synthetic nanoparticle of any one of embodiments 1-9, wherein the synthetic nanoparticle has a zeta potential between about 0 and about −5, 0 and about −4, or about −1 and about −3 in a solution of about pH 7.4.

Embodiment 11. The synthetic nanoparticle of any one of embodiments 1-10, wherein the synthetic nanoparticle has a zeta potential between about 1 and about 3 or about 2 and about 3 in a solution of about pH 6.5.

Embodiment 12. The synthetic nanoparticle of any one of embodiments 1-11, wherein the synthetic nanoparticle binds to scavenger receptor B-1 (SR-B1).

Embodiment 13. The synthetic nanoparticle of any one of embodiments 1-12, wherein the synthetic nanoparticle further comprises a nanostructure core on the interior of the pH sensitive liposome.

Embodiment 14. The synthetic nanoparticle of embodiment 13, wherein the nanostructure core comprises an organic nanostructure core.

Embodiment 15. The synthetic nanoparticle of embodiment 13, wherein the nanostructure core comprises an inorganic nanostructure core.

Embodiment 16. The synthetic nanoparticle of embodiment 13, wherein the nanostructure core comprises a gold nanostructure core.

Embodiment 17. A method of treating a subject who has cancer, comprising, administering an effective amount of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome.

Embodiment 18. The method of embodiment 17, wherein the synthetic nanoparticle is a nanoparticle of any one of embodiments 2-16.

Embodiment 19. The method of embodiment 17, wherein the cancer is selected from: B-cell lymphoma and T-cell lymphoma.

Embodiment 20. The method of any one of embodiments 17-19, wherein the cancer is comprised of SR-B1 positive cancer cells.

Embodiment 21. The method of any one of embodiments 17-20, wherein the cancer is comprised of SR-B1 negative cancer cells.

Embodiment 22. The method of any one of embodiments 17-21, wherein the drug is a chemotherapeutic agent.

Embodiment 23. The method of any one of embodiments 17-21, wherein the drug is Andro or derivatives thereof.

Embodiment 24. The method of any one of embodiments 17-21, wherein the effective amount of the nanoparticle comprises a sub-therapeutic amount of a drug, wherein a subtherapeutic amount comprises an amount that is less than a minimal amount required for producing a therapeutic result in a buffer or alcohol carrier.

Embodiment 25. A method of reducing, in a population of cells, the number of live cancer cells, the method comprising: contacting the cancer cells with a synthetic nanoparticle of any one of embodiments 1-16, wherein the synthetic nanoparticle is in an effective amount to induce apoptosis in the cancer cells.

Embodiment 26. A method of treating a subject who has a stroke or has suffered from a stroke, comprising, administering an effective amount of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome.

Embodiment 27. The method of embodiment 26, wherein the synthetic nanoparticle is a nanoparticle of any one of embodiments 2-16.

Embodiment 28. The method of embodiment 26, wherein the nanoparticle is administered to the subject within 1 month of the stroke in the subject.

Embodiment 29. The method of embodiment 26, wherein the nanoparticle is administered to the subject within 1 week of the stroke in the subject.

Embodiment 30. The method of embodiment 26, wherein the nanoparticle is administered to the subject within 1 day of the stroke in the subject.

Embodiment 31. The method of embodiment 26, wherein the nanoparticle is administered to the subject within 12 hours of the stroke in the subject.

Embodiment 32. The method of any one of embodiments 26 and 27-31, wherein the drug comprises an anti-inflammatory agent.

Embodiment 33. The method of any one of embodiments 26 and 27-31, wherein the drug is selected from the group consisting of anti-platelet drugs, anticoagulants, tissue plasminogen activator, statins, and blood pressure drugs.

Embodiment 34. A method for modulating an immune response in a subject, comprising, administering an effective amount to modulate an immune response of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome.

Embodiment 35. The method of embodiment 34, wherein the synthetic nanoparticle is a nanoparticle of any one of embodiments 2-16.

Embodiment 36. The method of any one of embodiment 34 or embodiment 35, wherein the synthetic nanoparticle enhances cytotoxic T cells, natural killer (NK) cells, phagocytosis, antibody-dependent cell-mediated cytotoxicity (ADCC), or a combination thereof.

Embodiment 37. A method of inhibiting viral activity in a subject, comprising, administering an effective amount to inhibit viral activity of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome.

Embodiment 38. The method of embodiment 37, wherein the synthetic nanoparticle is a nanoparticle of any one of embodiments 2-16.

Embodiment 39. The method of any one of embodiment 37 or embodiment 38, wherein the synthetic nanoparticle enhances cytotoxic T cells, natural killer (NK) cells, phagocytosis, antibody-dependent cell-mediated cytotoxicity (ADCC), or a combination thereof.

Embodiment 40. The method of any one of embodiment 37 or embodiments 38-39, wherein the subject has been infected by, or is at risk of being infected by, influenza A virus, hepatitis B virus, hepatitis C virus, Herpes simplex 1 virus, Epstein-Barr virus, human papilloma virus, human immunodeficiency virus, and/or Chikungunya virus.

Embodiment 41. A method of increasing macrophage activity in a subject, comprising, administering an effective amount to inhibit viral activity of a synthetic nanoparticle comprising: a pH sensitive liposome comprising a lipid layer comprising at least one pH sensitive lipid; an apolipoprotein in contact with the lipid layer; and a drug having a low water solubility encapsulated within the liposome.

Embodiment 42. The method of embodiment 41, wherein the synthetic nanoparticle is a nanoparticle of any one of embodiments 2-16.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

General Techniques

The practice of the subject matter of the disclosure will employ, unless otherwise indicated, conventional techniques of molecular biology (including recombinant techniques), microbiology, cell biology, biochemistry and immunology, which are within the skill of the art. Such techniques are explained fully in the literature, such as, but without limiting, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A synthetic nanoparticle comprising:

a pH sensitive liposome comprising a lipid layer comprising at least one pH sensitive (a) lipid;

(b) an apolipoprotein in contact with the lipid layer; and (c) a drug having a low water solubility encapsulated within the liposome; and wherein the pH sensitive liposome comprises octadecylamine-p (API-L-ASP) 10 ("pH-ADT").

2. The synthetic nanoparticle of claim 1, wherein apolipoprotein is apolipoprotein A-I (Apo-A1), apolipoprotein A-II, or apolipoprotein E.

3. The synthetic nanoparticle of claim 1, wherein the pH sensitive liposome comprises a pH sensitive phospholipid.

4. The synthetic nanoparticle of claim 1, wherein the pH sensitive liposome further comprises egg-phosphatidylcholine, lipids egg-phosphatidylcholine (EPC), 1,2-distearoyl-sn-glycero-3-phosphoethanolamine-N-[methoxy (polyethylene glycol)-2000] (DSPE-PEG2000), DSPE-PEG-Cy 5, and/or a combination thereof.

5. The synthetic nanoparticle of claim 1, wherein the synthetic nanoparticle has a largest cross-sectional dimension of less than or equal to 1000 nanometers (nm).

6. The synthetic nanoparticle of claim 1, wherein the drug is andrographolide and/or derivative thereof.

7. The synthetic nanoparticle of claim 1, wherein the synthetic nanoparticle has a zeta potential between about 0 and about −5, 0 and about −4, or about −1 and about −3 in a solution of about pH 7.4.

8. The synthetic nanoparticle of claim 1, wherein the synthetic nanoparticle binds to scavenger receptor B-1 (SR-B1).

9. The synthetic nanoparticle of claim 1, wherein the synthetic nanoparticle further comprises a nanostructure core on the interior of the pH sensitive liposome.

10. The synthetic nanoparticle of claim 9, wherein the nanostructure core comprises an organic nanostructure core or an inorganic nanostructure core.

11. A method of treating a subject who has cancer, comprising, administering an effective amount of the synthetic nanoparticle of claim 1.

12. The method of claim 11, wherein the cancer is selected from: B-cell lymphoma and T-cell lymphoma.

13. The method of claim 11, wherein the effective amount of the nanoparticle comprises a sub-therapeutic amount of a drug, wherein a sub-therapeutic amount comprises an amount that is less than a minimal amount required for producing a therapeutic result, optionally wherein the effective amount of the nanoparticle comprises a sub-therapeutic amount of a drug in a buffer or alcohol carrier.

14. A method of reducing, in a population of cells, the number of live cancer cells, the method comprising: contacting the cancer cells with a synthetic nanoparticle of claim 1, wherein the synthetic nanoparticle is in an effective amount to induce apoptosis in the cancer cells.

15. A method of treating a subject who has a stroke or has suffered from a stroke, comprising, administering an effective amount of the synthetic nanoparticle of claim 1 to the subject.

16. A method for modulating an immune response in a subject, comprising, administering to the subject an effective amount to modulate an immune response of the synthetic nanoparticle of claim 1.

17. A method of inhibiting viral activity in a subject, comprising, administering to the subject an effective amount to inhibit viral activity of the synthetic nanoparticle of claim 1.

18. A method of increasing macrophage activity in a subject, comprising, administering an effective amount to inhibit viral activity of the synthetic nanoparticle of claim 1.

* * * * *